(12) United States Patent
Grey et al.

(10) Patent No.: US 9,131,888 B2
(45) Date of Patent: Sep. 15, 2015

(54) METRICS AND ALGORITHMS FOR INTERPRETATION OF MUSCULAR USE

(76) Inventors: Alexander B. Grey, Campbell, CA (US); Violetta Georgiou, Morgan Hill, CA (US); Edward Frank Hejtmanek, San Jose, CA (US)

( * ) Notice: Subject to any disclaimer, the term of this patent is extended or adjusted under 35 U.S.C. 154(b) by 406 days.

(21) Appl. No.: 13/239,064

(22) Filed: Sep. 21, 2011

(65) Prior Publication Data

US 2012/0071732 A1    Mar. 22, 2012

Related U.S. Application Data

(60) Provisional application No. 61/385,038, filed on Sep. 21, 2010, provisional application No. 61/385,046, filed on Sep. 21, 2010, provisional application No. 61/385,048, filed on Sep. 21, 2010, provisional application No. 61/514,148, filed on Aug. 2, 2011, provisional application No. 61/385,053, filed on Sep. 21, 2010, provisional application No. 61/385,051, filed on Sep. 21, 2010, provisional application No. 61/385,049, filed on Sep. 21, 2010.

(51) Int. Cl.
| | |
|---|---|
| *A61B 5/00* | (2006.01) |
| *A61B 5/22* | (2006.01) |
| *A61B 5/0205* | (2006.01) |
| *A61B 5/0488* | (2006.01) |
| *G06F 19/00* | (2011.01) |
| *A61B 5/01* | (2006.01) |

(52) U.S. Cl.
CPC ............... *A61B 5/224* (2013.01); *A61B 5/0205* (2013.01); *A61B 5/0488* (2013.01); *G06F 19/345* (2013.01); *G06F 19/3481* (2013.01); *A61B 5/01* (2013.01)

(58) Field of Classification Search
USPC .......................... 600/300, 301, 372, 546, 595
See application file for complete search history.

(56) References Cited

U.S. PATENT DOCUMENTS

| | | | | |
|---|---|---|---|---|
| 5,349,963 | A * | 9/1994 | Eskelinen | 600/546 |
| 6,352,516 | B1 * | 3/2002 | Pozos et al. | 600/587 |
| 6,625,485 | B2 * | 9/2003 | Levendowski et al. | 600/544 |
| 7,110,809 | B2 * | 9/2006 | Nakada | 600/546 |

(Continued)

FOREIGN PATENT DOCUMENTS

KR    20000072178 A    12/2000

OTHER PUBLICATIONS

International Search Report dated Apr. 27, 2012 as received in related application No. PCT/US2011/052646.

(Continued)

*Primary Examiner* — William Thomson
*Assistant Examiner* — Bobby Soriano
(74) *Attorney, Agent, or Firm* — Nadesan Beck P.C.; David A Jones

(57) ABSTRACT

A muscle assessment method utilizing a computing system, surface electromyometry (sEMG) sensors, and other sensors to gather data for one or more subjects engaged in an activity through operably coupling the one or more sensors to the computing system, and directing a computing system to select one or more muscle assessment protocols related to a number of different metrics. For a user subject engaged in a physical activity, assessing muscle condition, the muscle activity, and statistically related averages provide information to the user and about muscle and whole body fitness.

30 Claims, 25 Drawing Sheets

(56) References Cited

U.S. PATENT DOCUMENTS

| | | | |
|---|---|---|---|
| 7,593,769 B1 | 9/2009 | Ettare | |
| 7,846,067 B2* | 12/2010 | Hanoun | 482/8 |
| 2001/0049482 A1* | 12/2001 | Pozos et al. | 600/587 |
| 2004/0097838 A1* | 5/2004 | Paske et al. | 600/587 |
| 2005/0283205 A1 | 12/2005 | Lee et al. | |
| 2006/0079800 A1* | 4/2006 | Martikka et al. | 600/546 |
| 2006/0161225 A1* | 7/2006 | Sormann et al. | 607/61 |
| 2007/0017531 A1* | 1/2007 | Large | 128/898 |
| 2007/0232869 A1* | 10/2007 | Kanzaki et al. | 600/300 |
| 2007/0249957 A1* | 10/2007 | Gentempo et al. | 600/546 |
| 2007/0276282 A1* | 11/2007 | Fukumura et al. | 600/546 |
| 2009/0299210 A1 | 12/2009 | Marcarian | |
| 2010/0185398 A1* | 7/2010 | Berns et al. | 702/19 |
| 2011/0118621 A1* | 5/2011 | Chu | 600/546 |
| 2012/0101395 A1* | 4/2012 | Fujita et al. | 600/508 |

OTHER PUBLICATIONS

Written Opinion of the International Searching Authority Report dated Apr. 27, 202 as received in related application No. PCT/US2011/052646.

* cited by examiner

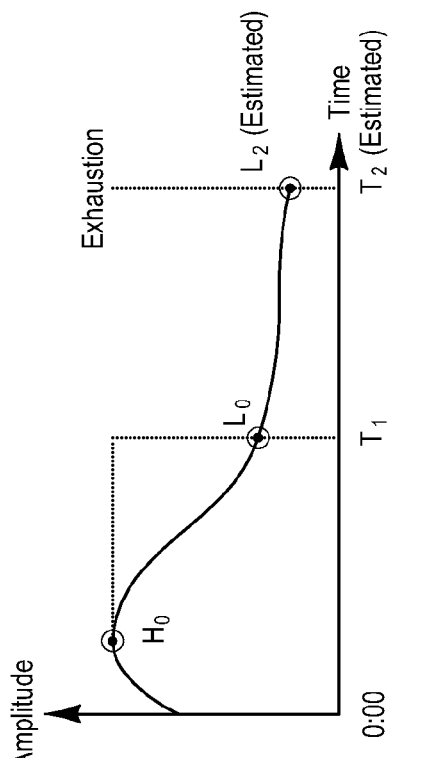
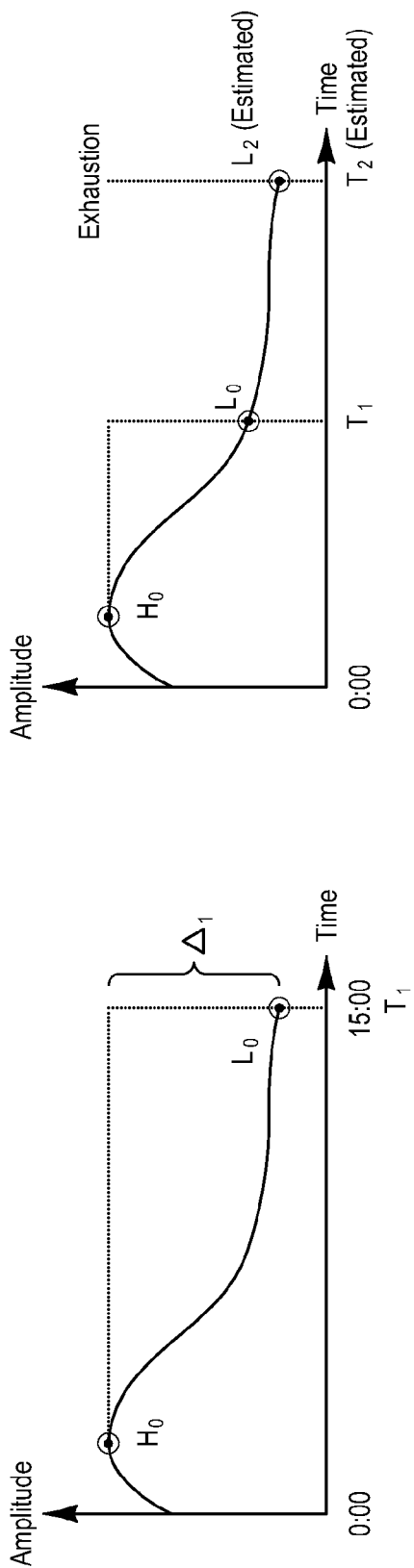
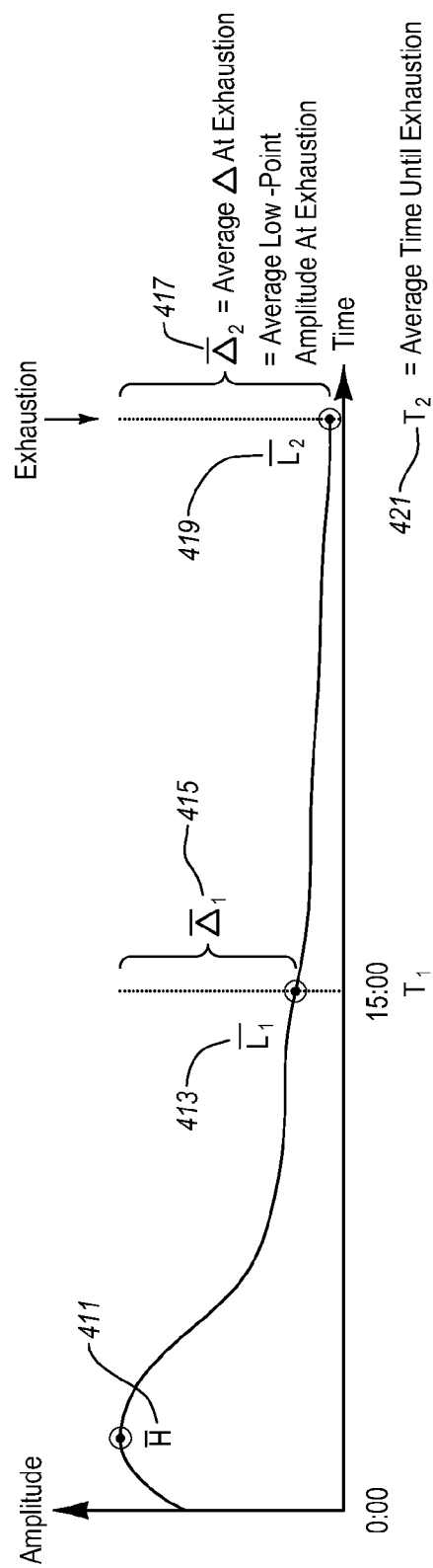

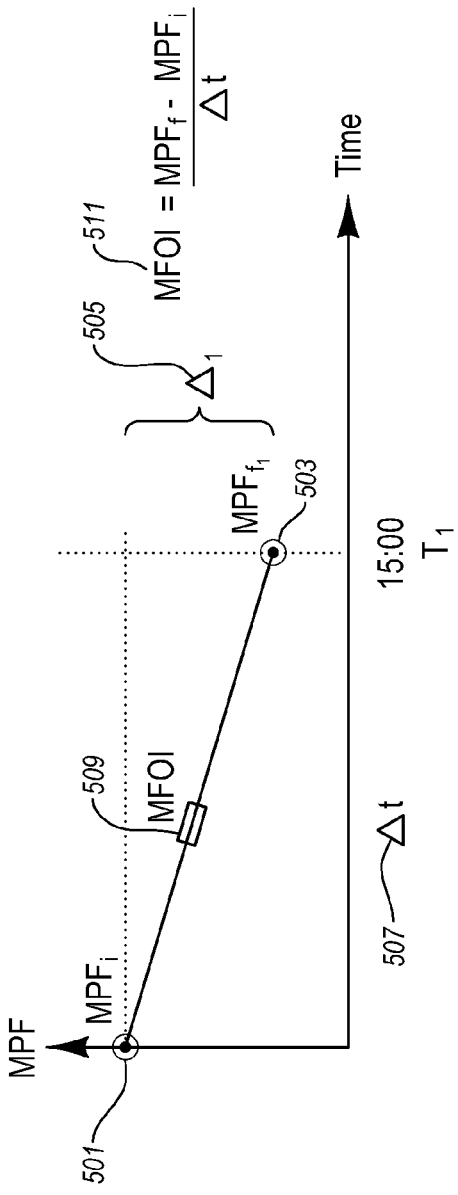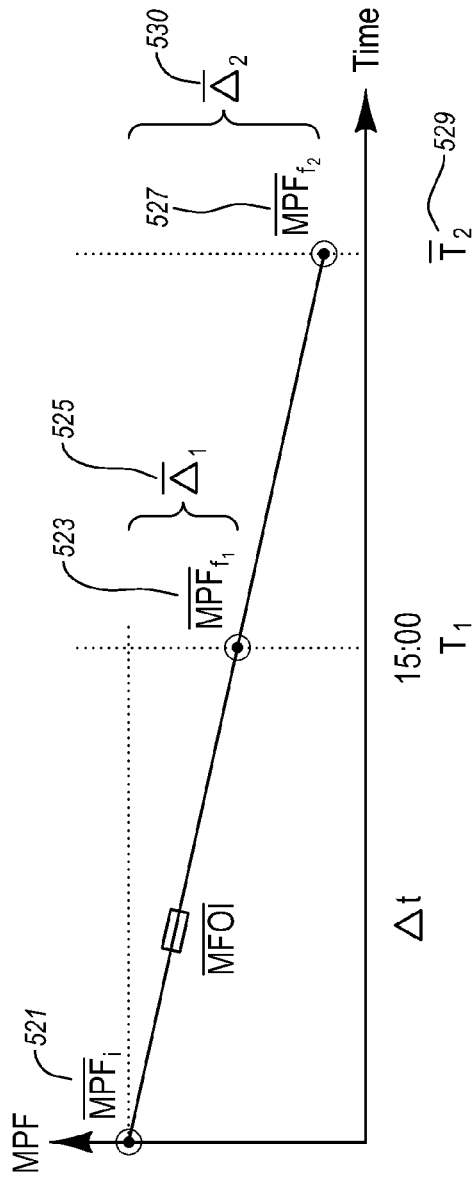

Integral SEMG:

$$I_S = \int_{t=0}^{t=Final} SEMG$$

Integral SEMG:

$$I_{S, NEW} = \int_{t=0}^{t=Final} SEMG_{NEW}$$

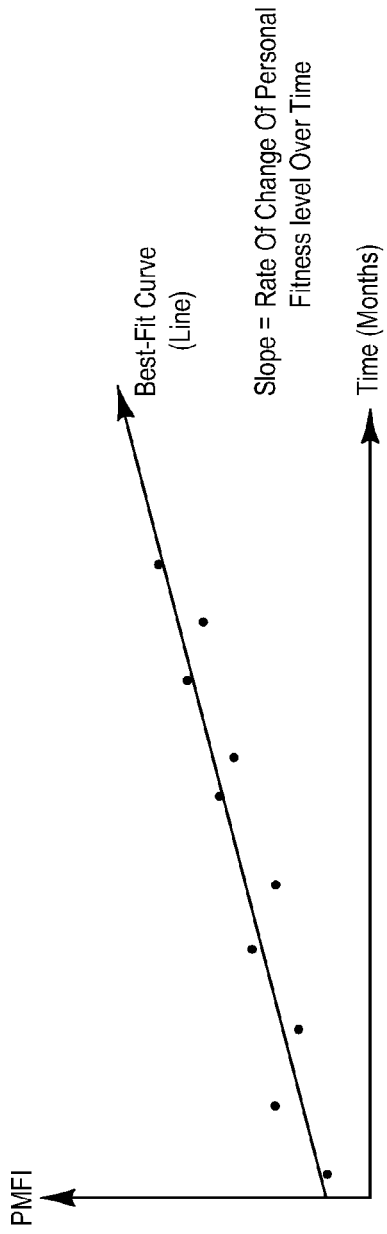
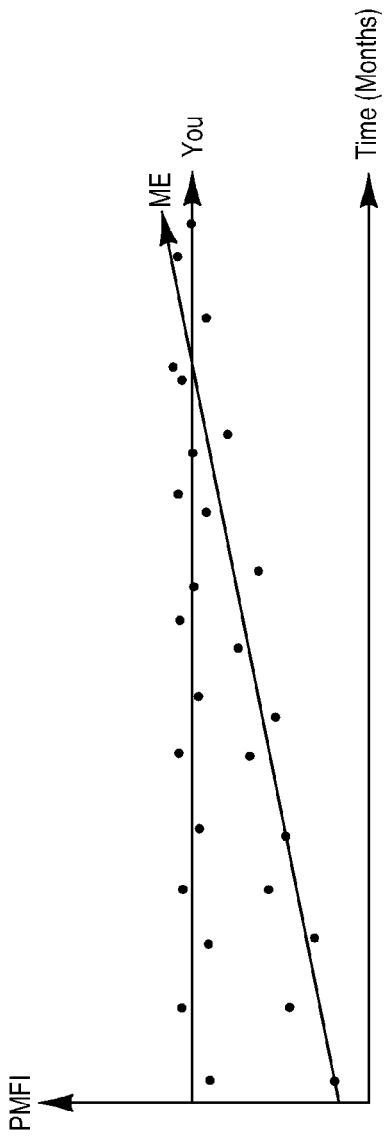

METRICS AND ALGORITHMS FOR INTERPRETATION OF MUSCULAR USE

CROSS-REFERENCE TO RELATED APPLICATIONS

This patent application claims the benefit of U.S. Provisional Application Nos. 61/385,046, 61/385,038, 61/385,048, 61/385,049, 61/385,051, and 61/385,053 all of which were filed on Sep. 21, 2010. In addition, this patent application claims the benefit of U.S. Provisional Application No. 61/514,148, filed Aug. 2, 2011. All of the aforementioned provisional applications are incorporated herein by specific reference in their entirety.

BACKGROUND OF THE INVENTION

Currently, various metrics are used to describe properties of muscular activation and function. Often, the measurement of muscle activation and function is measured by surface electromyography (sEMG), and analysis of the sEMG can include the following: the instantaneous root mean square amplitude (RMS), the average rectified amplitude, and the mean/median power frequency. The latter category can be referred to as an index of muscle fatigue. However, these currently available metrics are limited in ability to adequately characterize muscular activation. Additionally, these metrics are geared towards researchers and professionals for use in medical diagnoses. Certain qualities/quantities of muscle activation that are significant to athletic or average consumers have not yet been developed, and there is currently a lack of protocols to automatically generate these metrics.

The sEMG assessments can be sorted into three general groups of muscle activity: static muscle activity, dynamic muscle activity, or combination of static and dynamic muscle activities. The different muscle activity paradigms can be useful for different muscle assessments.

A static muscle activity may occur with no load (i.e. sitting) or with an isometric load (no movement of limb). Static muscle activity evaluation can include observation of the rectified amplitude of the sEMG data. The static muscle activity evaluation can be useful for a specific muscle or muscle group or as a comparison to other muscles or muscle groups. Absolute levels of the sEMG data can be monitored through the RMS of the sEMG amplitude (e.g., RMS of sEMG amplitude), and abnormally large values of the RMS sEMG can be identified or determined. Rhythmic contraction patterns of the muscle or muscle groups can be identified or determined, and may also be based on rectified amplitude. During an isometric loading protocol, a subject can exert an amount of force while keeping the limb fixed in a single position. Usually, the force exerted is measured as a fixed percentage of Maximum Voluntary Contraction (MVC). Then, the median frequency (MF) or mean power frequency (MPF) can be measured or determined by observing or analyzing the frequency spectrum of the sEMG. In this manner, the fatigue level of the muscles can be established, and the point at which fatigue begins to occur may be identified.

Dynamic muscle activity evaluations can ascertain relationships between sEMG amplitude and force, which have been shown to be "curvilinear", or non-linear at the extremes of the force range (e.g., very little force, or a lot of force) and essentially linear for the majority of the force/amplitude relationship. Evaluating that relationship is useful for dynamic muscle activity sEMG evaluation. Methods for implementing dynamic muscle activity evaluations can include incrementally increasing the force exerted by the muscle by way of a machine that measures force, and measuring the sEMG amplitude of the muscle activity that is associated with various force levels. Dynamic muscle activity evaluations can be used in the evaluation of torque and paralysis. There are dynamic muscle activity evaluation methods for: muscle imbalance, trigger points, cocontractions, and fasciculations.

However, the abovementioned muscle assessment methods can be used to assess a variety of pathologies and physiological states which may correspond to, or attempt to correspond to, clinical and/or medical conditions. These methods have typically been designed to be performed by specialists (e.g., MD, chiropractor, physical therapist, etc.). These muscle assessment methods are usually restricted to controlled settings in the presence of these specialists. Thus, there is not a way for a common person to implement muscular assessment on their own. Therefore, there remains a need to bring the ability to implement muscle assessment to the masses.

BRIEF DESCRIPTION OF THE DRAWINGS

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 4B is a depiction of sEMG data gathered to determine the CMOI conversion factor for a new subject on an amplitude vs. time graph with the maximum and minimum noted.

FIG. 4C is a depiction of the amplitude vs. time data for the average subject based on the related average dataset similar to the data gathered for the new subject, which when compared to the new subject data is used to create the CMOI conversion factor.

FIG. 4D is a depiction of estimated amplitude vs. time data based on the application of the CMOI conversion factor to the recorded new subject data.

FIG. 5B is a depiction of MPF vs. time data for the average subject based on the related average dataset similar to the data gathered for the new subject, which when compared to the new subject data is used to create the CMOI conversion factor.

FIG. 5C is a depiction of MPF vs. time data for the average subject based on the related average dataset similar to the data gathered for the new subject, which when compared to the new subject data is used to create the CMOI conversion factor.

FIG. 11A is a depiction of the rate of change of an individual's personal multi-dimensional fitness index (PMFI) index over time.

FIG. 11B is a depiction of the rate of change of one individual's PMFI over time compared to another individual's PMFI index over time.

Figure 1A:
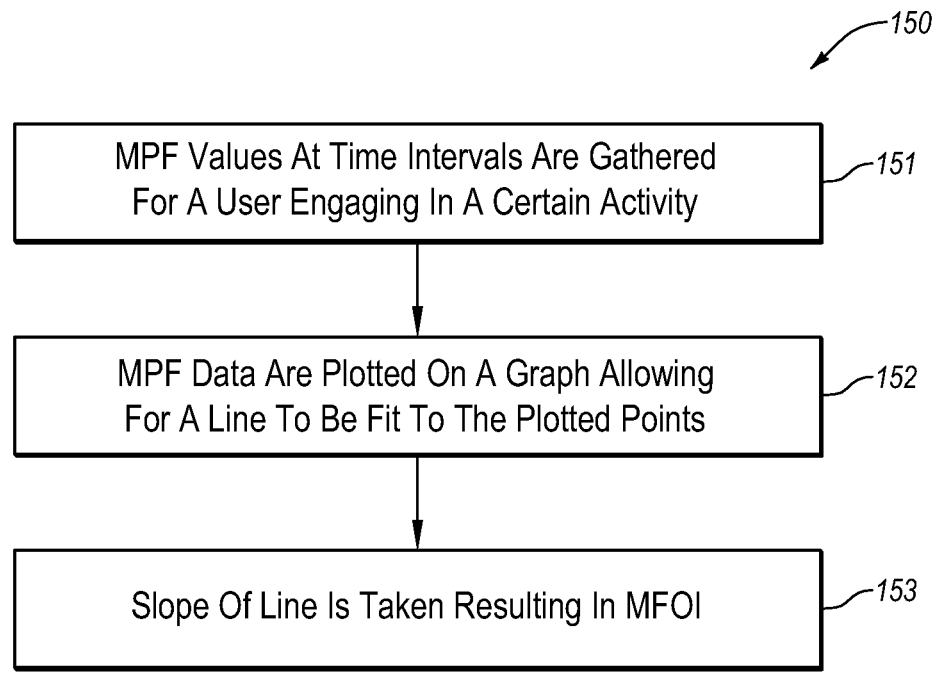
FIG. 1A is a depiction of the method of determining the muscle fatigue onset index (MFOI) conversion factor from the regular time interval graph.

These figures are arranged in accordance with at least one of the embodiments described herein, and which arrangement may be modified in accordance with the disclosure provided herein by one of ordinary skill in the art.

DETAILED DESCRIPTION OF THE PREFERRED EMBODIMENTS

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to systems and methods of implementing the assessment of muscle activation and performance by analyzing muscle data with algorithms and metrics. The term "subject" includes a user such as physical fitness consumer. The method can be utilized by a user to determine metrics useful in understanding the fitness of the user's own body alone, as compared to other user's metrics, and/or as compared to an average user's related metrics. There is described herein systems and methods including a computing system to gather a dataset of subject (e.g., a user of the system or method) who is engaged in an activity. The user's dataset is gathered, in part, from one or more of sensors or data gathering devices including: a surface electromyometry (sEMG) sensor attached to the skin of the user, temperature sensors attached to the user, heart rate sensors attached to the user, and the like. Each sensor or data gathering device is operably coupled to the computing system. The computing system then selects one or more muscle assessment protocols as directed by the user, automatically as determined by a predetermined decision, or even by a third party. The protocols selected will then configure the data necessary to properly determine the metric for the user engaged the activity, tailored for the activity, and the user. The metrics allow the user, or other third party, to assessing any of the following such as: the user's muscle condition, the user's muscle activity, a related average dataset based on average user's referenced in a database, projected estimates for the user's activity, and the like.

The computing system monitors and/or records relevant data of the users engaged in the activity. The computing system may also concurrently, or subsequently, monitor the data of other users engaged in the activity. Some metrics require a calibration period be used to gather data at ideal conditions for the user. In one embodiment, an ideal condition may be a 0° incline as opposed to a non-ideal condition such as a non-0° incline. The resulting metrics determine and assess the user's muscle activity as described above, but also are useful in determining a conversion factor to apply new estimates for activities performed under non-ideal conditions.

Often, the muscle data is provided as sEMG data, which can be processed by various algorithms in order to obtain metrics related to muscle activation and performance. The systems and methods can be designed to automatically calculate the metrics by sensors, processors, and computer-readable mediums. The systems can include hardware and software configured to perform the steps of the method described herein. For this invention, RMS amplitude can be described as an algorithm that is used to "rectify" a sEMG signal. If RMS is calculated, every data point (e.g., no "down sampling") effectively yields the absolute value of the incoming data points. The RMS amplitude, is a useful way of interpreting sEMG data coming from muscles. RMS can be used for many other kinds of interpretive analyses that may be performed with sEMG data. For instance, the average rectified value over a period of time can be calculated based on RMS data instead of using raw or raw and filtered data. RMS can also be used for the following amplitude based metrics described herein.

The methods of methods of implementing the assessment of muscle activation and performance can be performed with any subject. The subject can wear one or more sensors on one or more muscles that are going to be used during a muscle activity, where the sensors may or may not be operably coupled to a computing device that is also worn by the subject during the muscle activity. This computing device may record muscle data during the muscle activity, and it may also even have wireless access to a network and may be able to record the data on a server or database in real time. Additionally, the computing device that is capable of accessing a remote server or database over a network may be able to access muscle data or muscle activity metrics of other subjects that have performed a substantially similar muscle activity. The similarity of muscle activities can arise by the muscle activities being part of a predetermined muscle activity, which allows for comparison of muscle data and metrics across one or more populations of subjects. The other subjects can be filtered for physiological condition, size, weight, age or the like with respect to the subject that is primarily performing the muscle activity. The muscle data or metrics can be compared in real time with information provided to the subject engaged in the muscle activity on the fly, or the data and metrics can be saved and the comparison can be done with a computing system after completion of the predetermined muscle activity. The database may also be accessed for muscle data and metrics for the same subject so that they can compare the activation and function of a current predetermined activity with a past implementation of the predetermined activity.

The ability to access muscle data and metrics from a database can allow for the subject to statistically generate estimates of the muscle data and metrics that is useful for determining muscle condition. In general, the comparison between data gathered for the new subject and a related average dataset is used to generate a conversion factor. The conversion factor is useful in generating a number of different metrics as will be shown below. First, the computing device can gather a dataset for a new subject. This dataset can include both the new subject's primary sEMG data, such as the amplitude of the sEMG graph, the mean power frequency (MPF), the maximum voluntary contraction (MVC), the heart rate (HR), the temperature of the subject, and secondary data such as height, weight, type of activity, and the like. Once the data has been gathered for the new subject, the data can be plotted on a graph representing the new subject's current data. The computing device can then reference the database to determine a related average dataset. A related average dataset can be created from referencing a large number of statistically significant past measurements for other subjects. It is important to note that the related average dataset can account for the secondary data as well as primary data. The related average dataset may even be a prior implementation of the muscle activity of the same subject. The computing system can then determine a conversion factor based on the relationship of the new subject data to the related average dataset.

A conversion factor can provide information about the relationship of the subjects muscle condition compared to the other subjects muscle condition. A conversion factor can be determined for different metrics, alone or in combination, useful in analyzing the new subject's muscle activity and overall fitness level. The method for determining a conversion factor can be illustrated below.

In the descriptions of the embodiments below, the methods described herein can be used to perform useful estimations of muscle health, muscle condition, caloric burn, work performed, safety estimations, and the like. Frequently, the example of running is used. However, it should be understood that these indexes and algorithms can be applied to continuous muscle activities (e.g., bicycling, swimming, cycling, and the like) or noncontinuous muscle activities (e.g., weightlifting), as well as any number of other muscle activities that are conducive to sEMG-based analysis, which can be any static or dynamic muscle activity.

Muscle Fatigue Onset Index (MFOI)

The mean power frequency (MPF) can represent an average activation frequency of a muscular contraction, which can be measured during a short time period. Generally, the MFOI describes the rate of change of the MPF over a period of time. It has been shown that as a muscle becomes fatigued, the MPF decreases. However, the MPF alone may not be useful to a subject, and may not help the subject determine how "fit" their muscles are. This can be applied to overall condition of the muscles, not just how strong the muscles are, but more importantly the rate of change of the fatigue onset in their muscles. MFOI can be described as the average rate at which a muscle becomes fatigued. The MFOI and the MFOI conversion factor are muscle metrics that can be provided to individuals to assist in enhanced training for improvement of physical activities.

Thus, the MFOI is determined through MFOI protocol by selecting the MFOI protocol. As data is gathered, the MFOI protocol will configure data relevant to the MFOI metric such as the MPF, and duration. The data for MFOI can be gathered by measurements at set time intervals, continuously measuring peak amplitudes, continuously measuring average amplitudes, and the like. As the data is plotted to an MPF versus time graph, the slope of the line fitted to the data will determine the MFOI.

For example, a marathon runner who is in excellent shape may experience a very slow rate of muscle fatigue onset. On the other hand, an individual who is not in shape in terms of their muscular condition may experience a rapid rate of fatigue onset. The MFOI can allow for an easily comparable metric across individuals and populations that describe how quickly an average individuals' muscles become fatigued, and the MFOI conversion factor can allow for a new subject to estimate how quickly the new subject's muscles will become fatigued. Therefore MFOI and the MFOI conversion factor can be an important consideration for how "fit" the individual is.

The sensors worn by the subject can measure muscle data and determine metrics related to muscle activation and function. As such, various variables can be determined for the MFOI and the MFOI conversion factor. The frequency sampling rate (FSR) is an example of one variable in an algorithm for determining the MFOI and the MFOI conversion factor. The total length of time of the activity (AT) is another second variable. The quantity of total samples can be defined by Equation 1.

$$QS=(AT/FSR)+1 \quad \text{Equation 1}$$

FIG. 1A depicts a general method 150 of muscle assessment that can be used in determining the MFOI and the MFOI conversion factor. The method 150 can include: gathering MPF values for a subject engaging in a certain activity (block 151); plotting MPF values on a graph allowing for a line to be fitted to the plotted points (block 152); and determining the slope of the line, where the slope is the MFOI (block 153). The amplitudes of the movements are identified automatically by the computing device for each regular time interval from data obtained from the sensors associated with the muscles. The computing device can utilize hardware (e.g., processors) and software on computer-readable mediums configured to carry out the steps of the method 150 reflected in FIG. 1A, which can be implemented for determining MFOI and the MFOI conversion factor. When this data is compared to data in a database, an average MFOI associated with a related average dataset is determined. The MFOI conversion factor is determined by dividing the MFOI (block 153) by the average MFOI. The MFOI conversion factor is useful in assessing muscle fatigue onset of one subject compared to an average subject, and can estimate amplitudes over time for that subject.

Figure 1B:
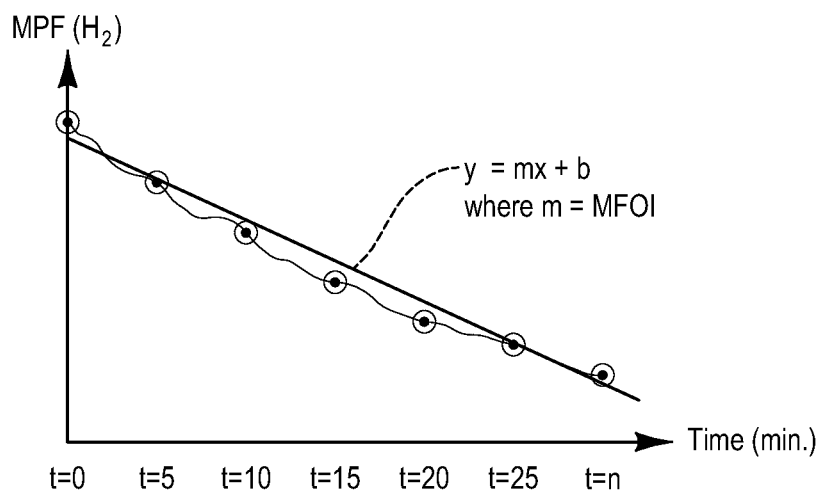
FIG. 1B is a depiction of sEMG data taken at regular intervals on a MPF vs. time.

For example, if an individual runs for 30 minutes, and the computing device samples MPF every 5 minutes, then 7 samples are taken (t=0, t=5, t=10, t=15, t=20, t=25, t=30) as shown in FIG. 1B. These 7 data points, which include a time-stamp as well as an associated MPF, can then be fit with a curve using one of a number of standard methods (e.g., linear, polynomial curves, etc.). As in FIG. 1B, for a simplest best-use scenario, a line can be fitted to the data points. Typically, a line is represented by the well-known equation of y=mx+b, where the variable "m" represents the slope of the line, and thus the MFOI. In FIG. 1, the line representing the plotted data, can have a non-positive slope. The slope of the line can be thought of as MFOI, which describes the subject's average rate of change of the MPF over time.

Figure 2A:
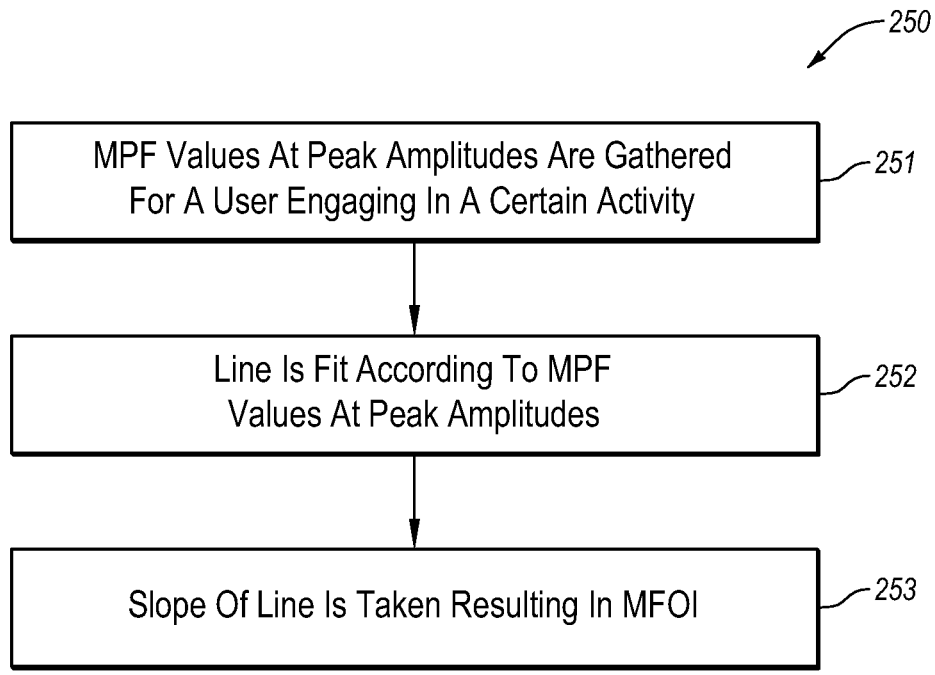
FIG. 2A is a depiction of the method of determining MFOI conversion factor with data taken continuously and fitting a line to maximum amplitudes recorded.
Figure 2B:
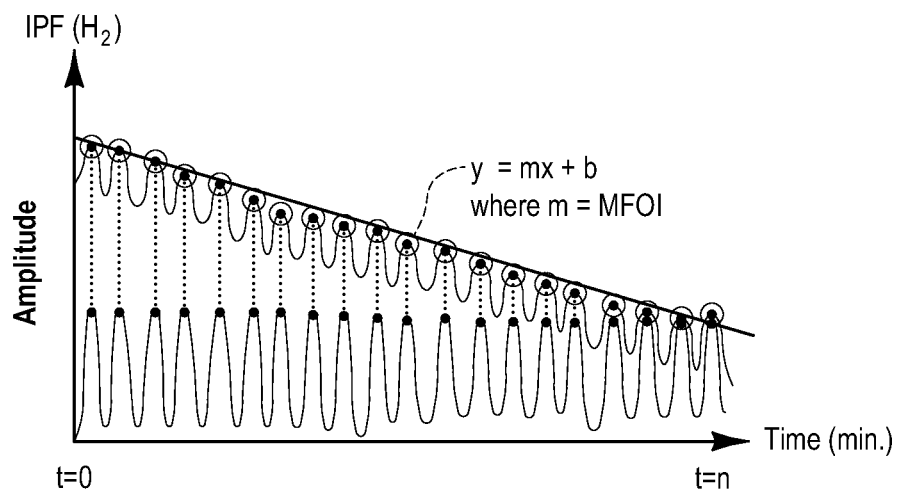
FIG. 2B is a depiction of sEMG data taken continuously, with the maximum amplitudes recorded and fitted to a line.

Another implementation of MFOI can be performed in which for regular periodic movement (e.g., such as running, bicycling, swimming, or weightlifting) the peak amplitudes of these regular movements are identified automatically by the computing device from data obtained from the sensors associated with the muscles. The computing device can utilize hardware (e.g., processors) and software on computer-readable mediums configured to carry out the steps of the method 250 reflected in FIG. 2A, which can be implemented for determining MFOI with periodic movement data and peak amplitudes. In the method 250: the MPF values at peak amplitudes are gathered for a subject engaging in a certain activity (block 251); a graph is generated and a line is fit according to the MPF values at peak amplitudes (block 252); and the slope of the line is taken resulting in MFOI (block 253). The graph and line thereof are illustrated in FIG. 2B.

Figure 3A:
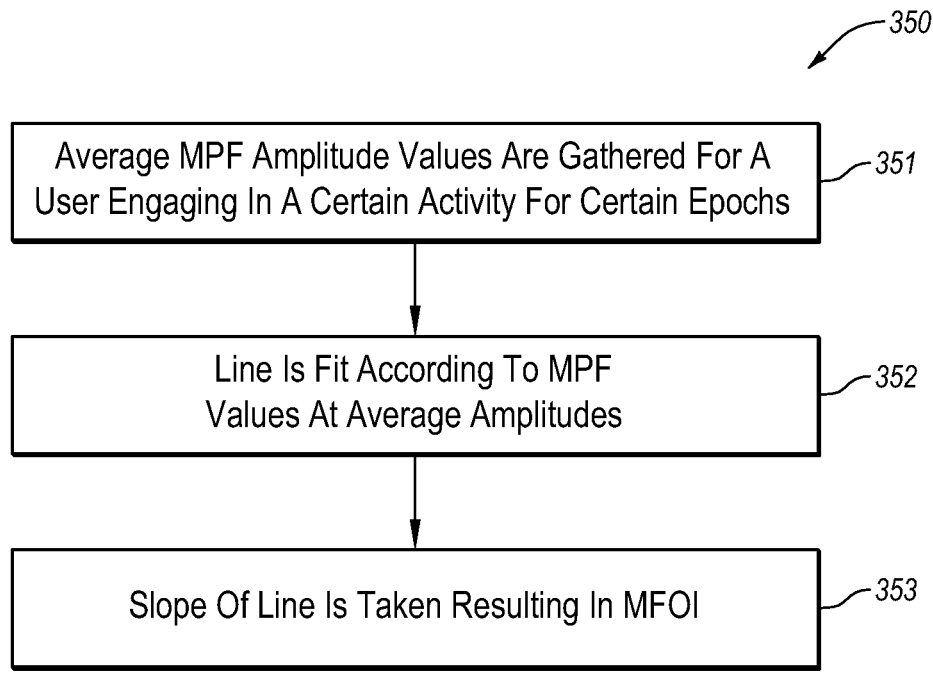
FIG. 3A is a depiction of the method of determining MFOI conversion factor with data taken continuously and fitting a line to the average amplitudes recorded per interval of time.
Figure 3B:
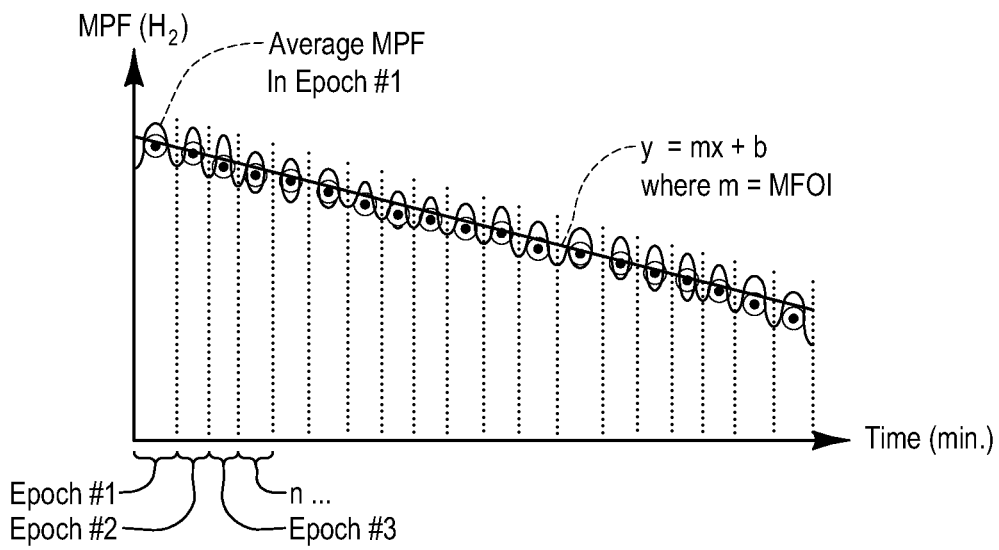
FIG. 3B is a depiction of sEMG data taken continuously, with the average amplitudes per interval of time recorded and fitted to a line.

Another implementation for obtaining MFOI and the MFOI conversion factor can be performed in which for regular periodic movement (e.g., such as running, bicycling, swimming, or weightlifting) the averaged MPF in pre-set epochs can be used compared with FSR in which periodic samples are taken from a larger data set. This can be conducted in a method 350 for determining a subject's average MFOI and the MFOI conversion factor with periodic movement, which is illustrated in FIG. 3A. In the method 350: the average MPF amplitudes are gathered for a subject engaging in a certain activity for certain epochs (block 351; a graph is generated and a line is fit according to MPF values at average amplitudes (block 352); and the slope of the line is taken resulting in MFOI (block 353).

For all of the aforementioned methods, the MFOI conversion factor may be determined by referencing a database to determine a related average dataset. Thus, the method for determining the MFOI conversion factor for the method 250 and the method 350 is the same as the method for determining the MFOI conversion factor described above in method 150.

In general, the conversion factor is determined by a computing device gathering a dataset for a new subject. Once data has been gathered, a graph is generated and a line or a curve is fit according the data associated with each metric. Significant data values can be derived from the graph. In some metrics, such as MFOI, the significant data value is the slope of the line. In other metrics, significant data values may be the initial maximum amplitude, the final amplitude, the difference between the values, the work done by the activity, the temperature of the subject, the heart rate of the subject, the maximum voluntary contraction, the median power frequency, the mean frequency, any combination of the aforementioned values, and the like. Once significant values are determined, a database is referenced that determines a related average dataset. The conversion factor is based on the relationship between a subject's dataset and a related average dataset. In general, a conversion factor can be associated with any of the following, or aforementioned, metrics to assess muscular activity, alone or in combination.

The MFOI methods include the utilization of the MPF. Additionally, the MFOI can include the MPF in conjunction with amplitude values (e.g., combination terms which take the amplitude, and then add a term which utilizes the MPF or rate of change of the MPF). So if the amplitude is A, and the rate of change of the MPF is R, then the term for the combination method could be: A*c1+R*c2, where c1 and c2 are constants determined through database comparison or through past data recorded from the user, or a combination of both.

Additionally, in MFOI another embodiment can include taking particular slices of the frequency spectrum, and use those slices in the calculation of the MPF. This can be done instead of taking the whole frequency range to produce the MPF. For instance, if measuring from 50-500 Hz for sEMG, the MPF can be calculated based only upon 80 Hz-150 Hz. Alternatively, it can be calculated based on two regions (e.g., 20-40 Hz and 80-150 Hz), where each MPF calculation from each frequency range is multiplied by a constant which assigns significance. Other manipulations to frequency domain can be performed to produce more complex versions of a frequency characterization.

Chronic Muscle Overuse Index (CMOI)

It is known that exercising or engaging in a physical activity when an individual's muscles are fatigued can contribute to injury. It is also known that there are a number of different variables (e.g., individual physiological characteristics) that contribute to the rate of muscular fatigue onset, such as muscle length, local chemical characteristics, conduction velocity, and how "in shape" the individual is. In order to take these known variables, and use them in a way that can help prevent injury, a chronic muscle overuse index (CMOI). There are at least two categories of algorithmic protocols which may be used to determine a CMOI: amplitude-based CMOI calculation, and frequency-based CMOI calculation. In the following examples, calculations of CMOI will be performed for distance-running types of exercise; however other continuous or noncontinuous muscle activities can be performed for an CMOI protocol.

CMOI protocol can include an initial calibration where the user engages in an activity under ideal conditions. As data is gathered, the CMOI protocol will configure data relevant to the CMOI metric such as the sEMG amplitude, sEMG MPF, and duration. CMOI can be calculated by either the amplitude data gathered or by MPF data gathered. The data is plotted to either amplitude versus time graph, or MPF versus time graph. The CMOI protocol determines an average related dataset by referencing a database of other average users. CMOI is then developed based on the relationship between the dataset and the related average dataset. Finally, a conversion factor is found to determine CMOI for a non-ideal condition.

Figure 4A:
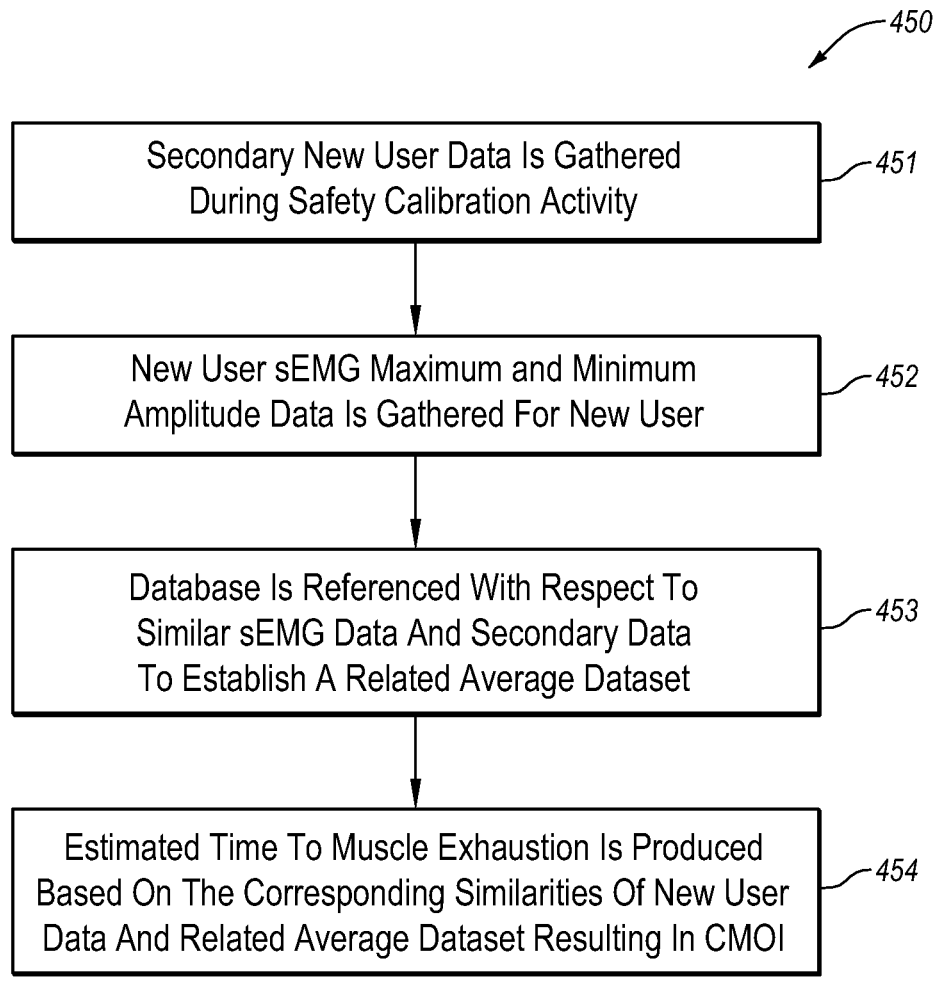
FIG. 4A is a depiction of the method for determining the chronic muscle overuse index (CMOI) conversion factor using amplitude values to aid the subject in preventing injury by estimating a time beyond which it is more likely for a subject to experience an injury.

In an example of amplitude-based CMOI and CMOI conversion factor calculation, a new subject first conducts a safe calibration run for a short time at a slow/moderate speed in a controlled environment (e.g., for example: treadmill, 15:00 minutes, 4.0 mph, 0° incline). A method 450 of calculating an amplitude-based CMOI is illustrated in FIG. 4A. Initially, secondary subject data are gathered prior to or during a calibration run (block 451). The new subject performs a calibration run during which maximum and minimum amplitude data is gathered (block 452). The data is then referenced with respect to similar data of a database to establish a related average dataset (block 453). The CMOI is calculated based on similarities of the new subject data collected during the calibration run compared to the related average dataset (block 454). This CMOI helps to estimate the time to exhaustion the new subject will experience for subsequent runs. However, this can be performed for any muscle activity.

FIG. 4B graphically shows how the calculations are performed. The amplitude high-point for this segment is recorded as $H_0$, the low-point is saved as $L_0$, and the difference between the two is assigned to $\Delta_1$. Next, a database is referenced with respect to similar data including primary and secondary data such as demographics (e.g., subject age, height, weight, activity type, muscle in question) to obtain a similar CMOI and/or similar $\Delta_1$. As shown graphically in FIG. 4C, the database returns a number of datasets (e.g., at least 35 datasets for statistical significance), which together produce a number of average values: $H_{(average)}$ 411, $L_{1(average)}$ 413, $\Delta_{1(average)}$ 415, $\Delta_{2(average)}$ 417, $L_{2(average)}$ 419, $T_{2(average)}$ 421. $H_{(average)}$ 411 is the average high-point amplitude of subjects in the database. $L_{1(average)}$ 413 is the average low-point amplitude of subjects in the database. $\Delta_{1(average)}$ 415 is the difference between $H_{(average)}$ 411 and $L_{1(average)}$ 413. $T_{2(average)}$ 421 is the time at which subjects in the database experience perceived muscular exhaustion, and/or observable loss of coordination. Likewise, $L_{2(average)}$ 419 is the amplitude at which subjects in the database experienced perceived muscular exhaustion, and/or observable loss of coordination. $\Delta_{2(average)}$ 417 is the difference between $H_{(average)}$ 411 and $L_{2(average)}$ 419.

Then as shown in FIG. 4D, $L_{2(estimated)}$ 431 is calculated by Equation 2.

$$L_{2(estimated)} = H_0 - \Delta_{2(average)} \qquad \text{Equation 2}$$

$T_{2(estimated)}$ 433 is also calculated by Equation 3.

$$T_{2(estimated)} = T_{2(average)} = ((\Sigma_{n=0}^{n} T_2)/n) \qquad \text{Equation 3}$$

Figure 5A:
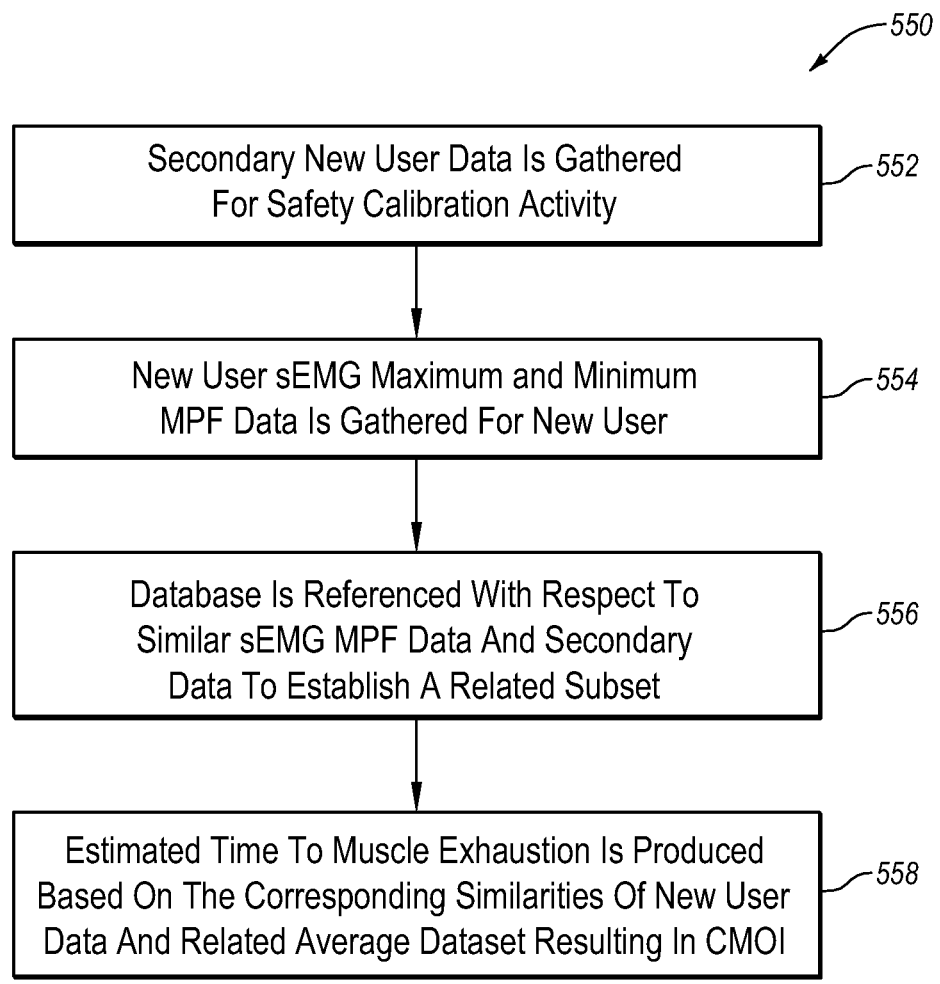
FIG. 5A is a depiction of the method for determining the CMOI conversion factor using mean power frequency (MPF) values to aid the subject in preventing injury by estimating a time beyond which it is more likely for a subject to experience an injury.
Figure 5D:
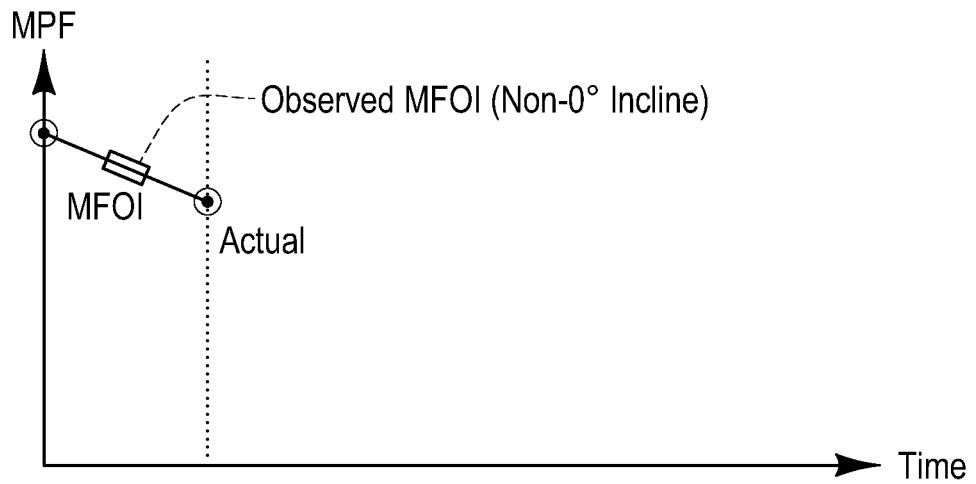
FIG. 5D is a depiction of the rate of change for non-ideal conditions on the MPF vs. time graph.
Figure 5E:
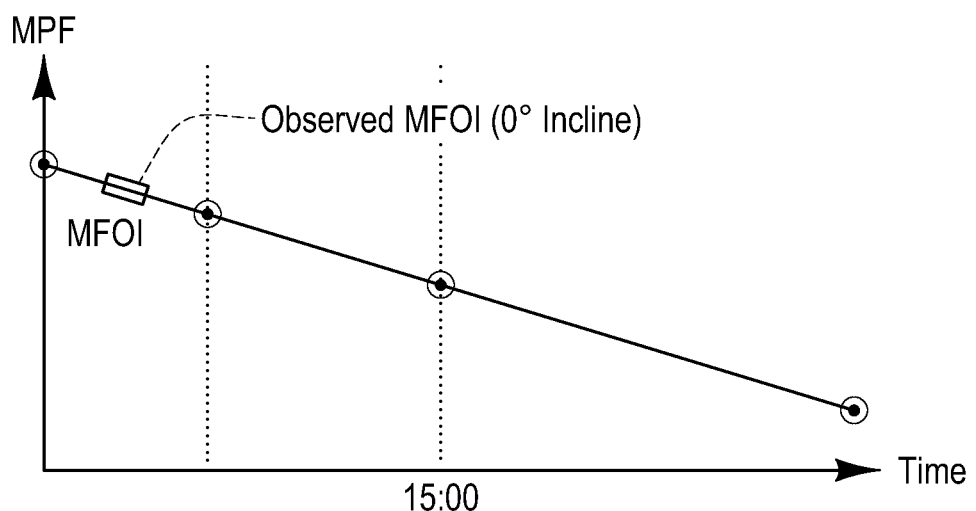
FIG. 5E is a depiction of the rate of change for ideal conditions on the MPF vs. time graph.

In a frequency-based CMOI calculation, a new subject first conducts a safe calibration run for a short time at a slow/moderate speed in a controlled environment (for example: treadmill, 15:00 minutes, 4.0 mph, 0° incline). A muscle assessment method 550 can be conducted as described in order to determine a CMOI, which method is shown in FIG. 5A. The secondary new subject data is gathered such as subject age, height, weight, activity type, or the like (block 552). The new subject primary data, including maximum and minimum MPF data, is gathered during a calibration activity (block 554). The database for the muscle activity is referenced to identify and/or obtain data for others that have similar demographics and/or similar CMOI in order to establish a related average dataset (block 555). The estimated time to muscle exhaustion is produced based on the corresponding similarities of new subject data and the related average dataset (block 558).

The data obtained during the method 550 can be used to produce the CMOI frequency based metrics that are graphically represented in FIGS. 5B-5E. As shown in FIG. 5B, the calibration run produces the maximum frequency ($MPF_i$) 501, a final/minimum frequency ($MPF_f$) 503, the difference between the $MPF_i$ and the $MPF_f$ ($\Delta_2$) 505, the time change ($\Delta t$) 507, and the MFOI 509 represented by the MFOI equation 511.

As discussed above, the database is referenced to build an average dataset that is similar to the data gathered. The database returns some number of datasets (e.g., at least 35 data sets for statistical significance). As shown in FIG. 5C, the database referencing produces a number of average values: $MPF_{i(average)}$ 521, $MPF_{f1(average)}$ 523, $\Delta_{1(average)}$ 525, $MPF_{f2(average)}$ 527, $T_{2(average)}$ 529, $\Delta_{2(average)}$ 531.

$MPF_{i(average)}$ 521 is the average high-point MPF of subjects in the database. $MPF_{f1(average)}$ 523 is the average low-point MPF of subjects in the database. $\Delta_{1(average)}$ 525 is the difference between $MPF_{i(average)}$ 521 and $MPF_{f1(average)}$ 523. $T_{2(average)}$ 529 is the time at which subjects in the database experience perceived muscular exhaustion, and/or observable loss of coordination. Likewise, $MPF_{f2(average)}$ 527 is the amplitude at which subjects in the database experienced perceived muscular exhaustion, and/or observable loss of coordination. $\Delta_{2(average)}$ 531 is the difference between $MPF_{i(average)}$ 521 and $MPF_{f2(average)}$ 527.

Figure 5F:
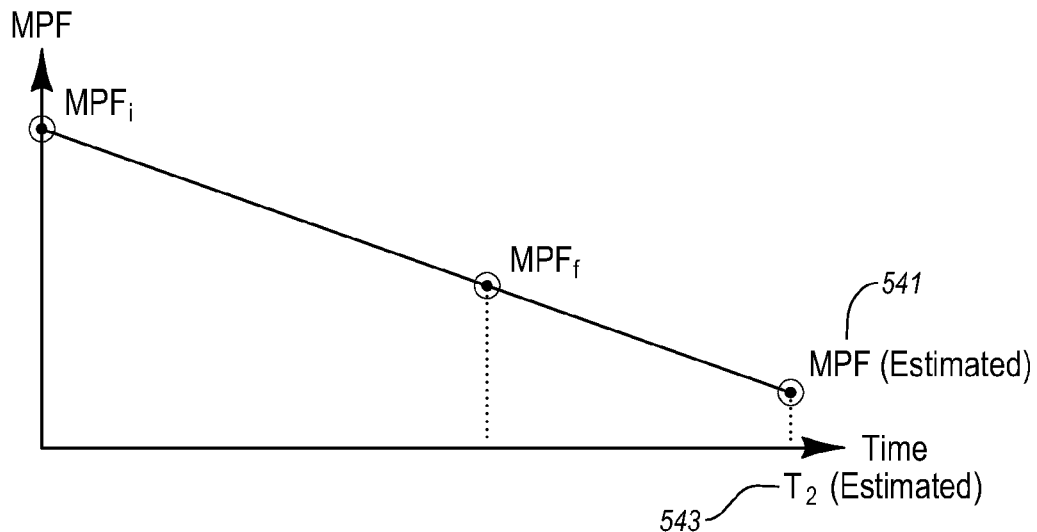
FIG. 5F is a depiction of the MPF vs. time graph used to determine an estimated time to muscle exhaustion based on the application of the frequency based CMOI conversion factor to the new subject data.

Turning to FIG. 5F, $MPF_{2(estimated)}$ 541 is then calculated for the new subject. $MPF_{2(estimated)}$ 541 is the estimated MPF at which the new subject will experience muscular exhaustion, and is calculated by Equation 4. In Equation 4, $T_2$ is the time associated with an individual subject entry in the database.

$$MPF_{2(estimated)} = MPF_1 - \Delta_{2(average)} \qquad \text{Equation 4}$$

$T_{2(estimated)}$ 543, the estimated time to new subject exhaustion, is defined by Equation 5.

$$T_{2(estimated)} = T_{2(average)} = ((\Sigma_{n=0}^{n} T_2)/n) \qquad \text{Equation 5}$$

Figure 5G:
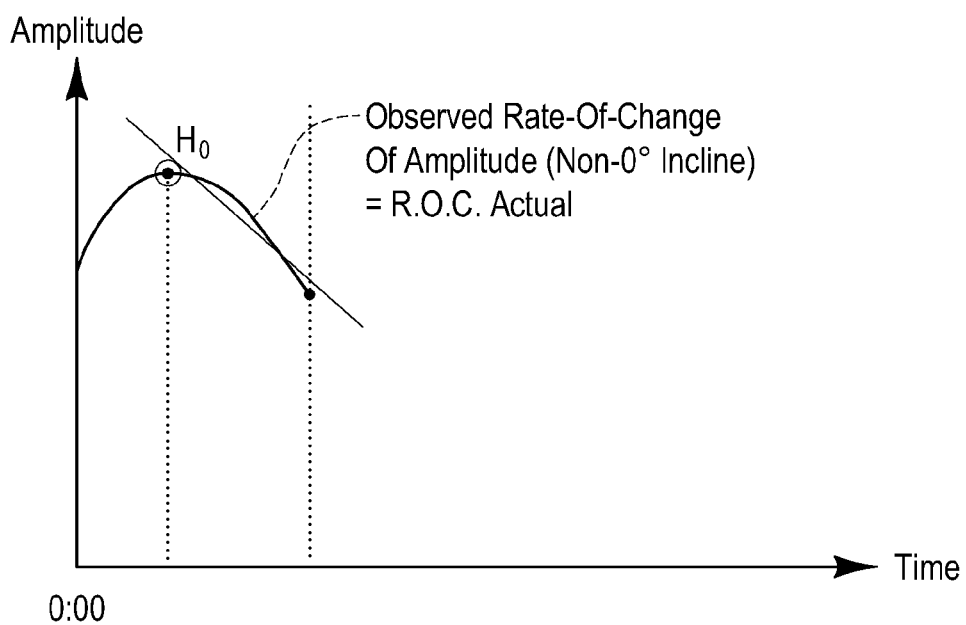
FIG. 5G is a depiction of the rate of change for non-ideal conditions on the amplitude vs. time graph for determining the amplitude based CMOI conversion factor.
Figure 5H:
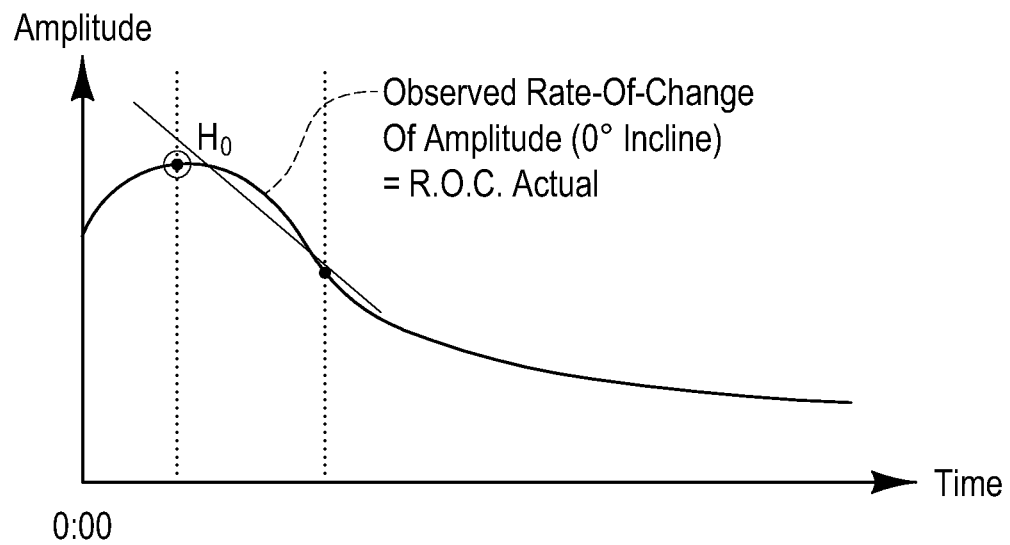
FIG. 5H is a depiction of the rate of change for non-ideal conditions on the amplitude vs. time graph used to determine a conversion factor and estimated time to muscle exhaustion based on the application to the new subject data.

Subsequently, with any amplitude an observed rate of change can be calculated, and a CMOI conversion factor can be calculated. This rate of change can then be used to calculate times to exhaustion for subsequent activities of the same subject, even under differing conditions. For instance, as shown in FIGS. 5G and 5H for amplitude data, the observed rate of change can be observed for either a 0° incline or a non-0° incline, allowing for a conversion factor to be generated. This conversion factor can be adjusted for variables in the physical environment, which cause the subject to fatigue faster than expected. One method of doing this is based on the observed rate of change (ROC) of amplitude. For example, the rate of change on a non-0° incline $ROC_{actual}$, which when divided by the observed rate of change of amplitude $ROC0°$ (for 0° incline), produces the desired conversion factor. This conversion factor can be regularly recalculated by Equation 6.

$$\text{Conversion Factor} = ROC_{actual}/ROC0° \qquad \text{Equation 6}$$

From there, the estimated time of exhaustion may be calculated from the information previously provided by the related average dataset, and as explained when calculating the safety zones discussed below.

Figure 5I:
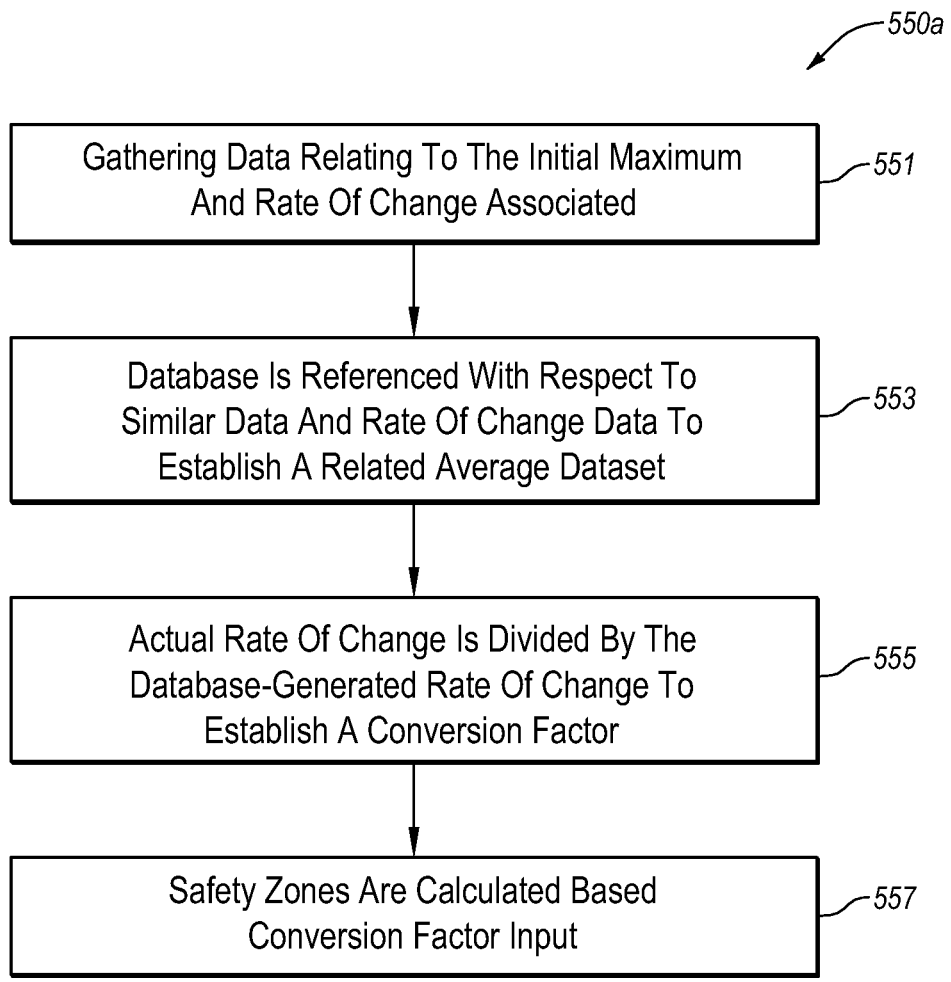
FIG. 5I is a depiction of the method for determining the estimated time to muscle exhaustion based on the relationship between the actual rate of change observed and the rate of change of the related average dataset.

In both the amplitude-based, and the frequency-based calculation, "safety zones" can be established using the amplitude or MPF ranges for each zone, and the times associated with the boundaries for each zone. These zones can be visualization aids and are, in one embodiment, displayed on a graphical subject interface, and essentially break down the MPF range (from T=0 until final average MPF at the exhaustion point for the relevant database subset that is returned) into a number of easy-to-visualize categories. The method for creating these zones is explained shown in FIG. 5I. The relevant data is gathered by measuring maximum values (block 551). The database is referenced with respect to similar data to establish a related average dataset (block 553). The actual rate of change is divided by the related average dataset rate of change to establish a conversion factor (block 555). Safety zones are calculated based on the conversion factor as input (block 557). In addition, because these estimated zones are associated with either an amplitude or a frequency, the corresponding times can be calculated for these times zones. These visualization aids essentially break down the amplitude range (e.g., from start until final average amplitude at the exhaustion point for the relevant database subset that is returned) into a number of easy-to-visualize categories. In one embodiment, this may be done in a color code that is intuitive to subjects, such as Green, Yellow, Orange, and Red.

Figure 5J:
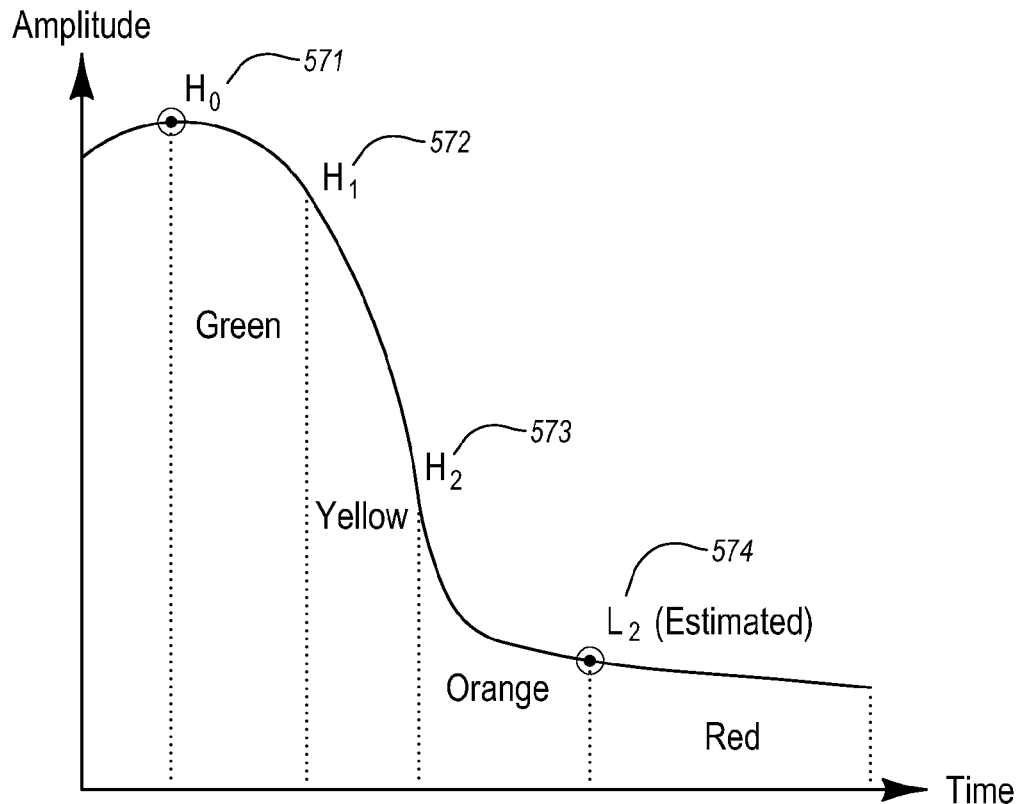
FIG. 5J is a depiction of the amplitude vs. time graph and the safety zones developed from the data gathered in the amplitude based CMOI method to aid the subject in preventing injury.

For an amplitude based calculation shown in FIG. 5J, the Green Zone can begin at $H_0$ 571 and continues until, but not including, $H_1$ 572 calculated by Equation 7.

$$H_1 = [H_0 - (H_0 - L_{2(estimated)})/3] \qquad \text{Equation 7}$$

The Yellow Zone begins at $H_1$ 572, but not including and continues until, but not including, $H_2$ 573 calculated by Equation 8.

$$H_2 = [H_1 - (2*(H_0 - L_{2(estimated)})/3)] \qquad \text{Equation 8}$$

The Orange Zone begins at $H_2$ 573 and continues until, but not including, $L_{2(estimated)}$ 574 as calculated by the equation listed above in Equation 2. It should be noted that the present invention contemplates a plurality of zones as required by the subject represented by Equation 9.

$$H_{(n+1)} = [H_n - ((n+1)*(H_0 - L_{2(estimated)})/3)] \qquad \text{Equation 9}$$

The Red Zone is any amplitude greater than or equal to $L_{2(estimated)}$ 574. Finally, these amplitude divisions corresponding to safety zones may be converted to estimate times for each zone.

Figure 5K:
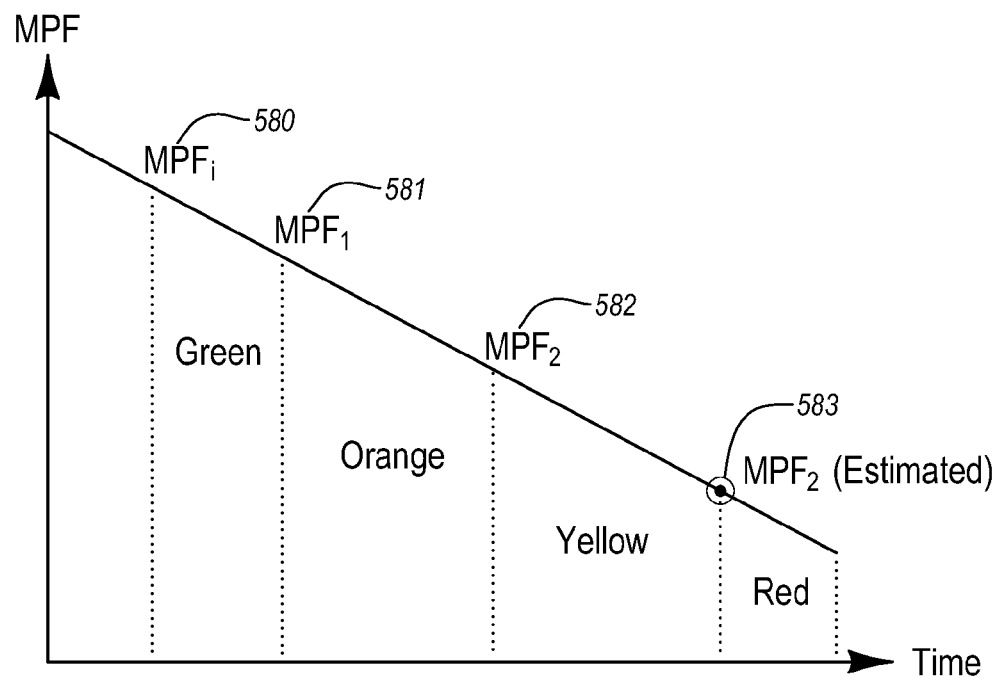
FIG. 5K is a depiction of the MPF vs. time graph and the safety zones developed from the data gathered in the frequency based CMOI method to aid the subject in preventing injury.

For an MPF based calculation shown in FIG. 5K, the Green Zone begins at $MPF_i$ 580 and continues until, but not including, $MPF_1$ 581 calculated by Equation 10.

$$MPF_1 = [MPF_i - (MPF_i - MPF_{2(estimated)})/3] \qquad \text{Equation 10}$$

The Yellow Zone begins at $MPF_1$ 581 and continues until, but not including, $MPF_2$ 582 calculated by Equation 10a.

$$MPF_2 = [MPF_1 - (2*(MPF_i - MPF_{2(estimated)})/3)] \qquad \text{Equation 10a}$$

The Orange Zone begins at $MPF_2$ 582 and continues until, but not including, $MPF_{2(estimated)}$ 583 calculated by Equation 2. It should be noted that the present invention contemplates a plurality of zones as required by the subject represented by Equation 10b.

$$MPF_{(n+1)} = [MPF_n - ((n+1)*(MPF_i - MPF_{2(estimated)})/3)] \qquad \text{Equation 10b}$$

Finally, these MPF divisions corresponding to safety zones may be converted to estimate times for each zone. Additionally, the estimated time of exhaustion, $T_{2(estimated)}$, may be calculated from the information provided from calculating the safety zones.

Like in the amplitude-based calculation, a conversion factor can be calculated for subsequent activities during a frequency-based calculation as in FIG. 5B and FIG. 5C. This conversion factor would adjust for variables in the physical environment which cause the subject to fatigue faster than expected. One method of doing this is based on the observed rate of change (ROC) of MPF, or aka the MFOI. For example, the rate of change on a non-0° incline $ROC_{actual}$, which when divided by the observed rate of change of amplitude $ROC_0°$ (for 0° incline), produces the desired conversion factor. This conversion factor can be regularly recalculated by Equation 10c.

$$\text{Conversion Factor} = ROC_{actual}/ROC_0° \qquad \text{Equation 10c}$$

Warm-Up Index (WUI)

Some athletes know the amount of time it takes them to warm up thoroughly based on years of trial and error experiences. However, the development of a warm-up index (WUI) can be used instead of the need for determination of this safety point through trial and error. While there are a multitude of factors that contribute to the length of time necessary to become warmed up, (e.g., including the muscles being exercised, general cardiovascular condition, etc.), the WUI should enable novice subjects to be better equipped to exercise and to understand their muscle response patterns more easily.

Figure 7A:
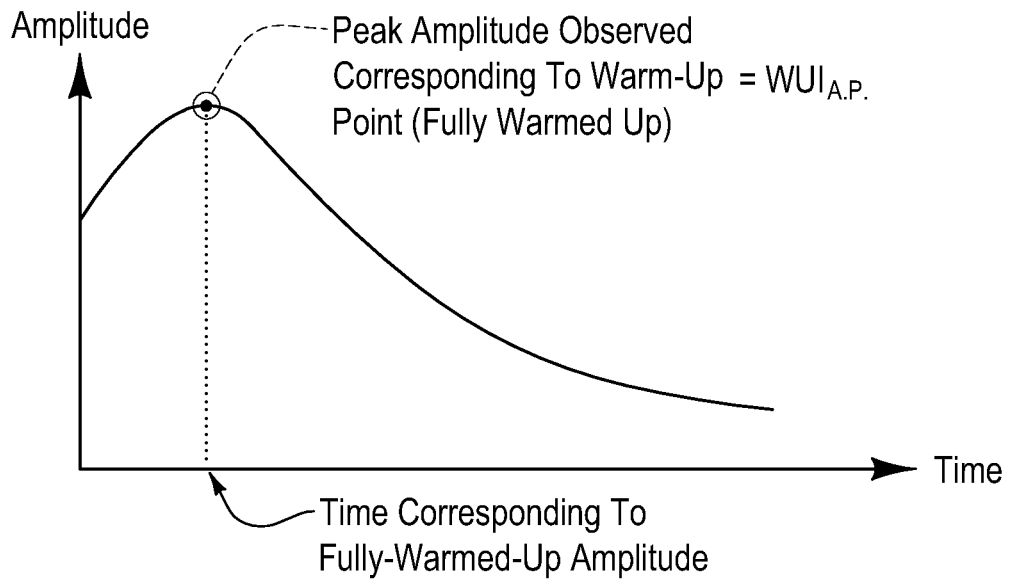
FIG. 7A is a depiction of the amplitude vs. time graph where the peak amplitude of the new subject data is used to determine a first warm-up indicator in creating.
Figure 7B:
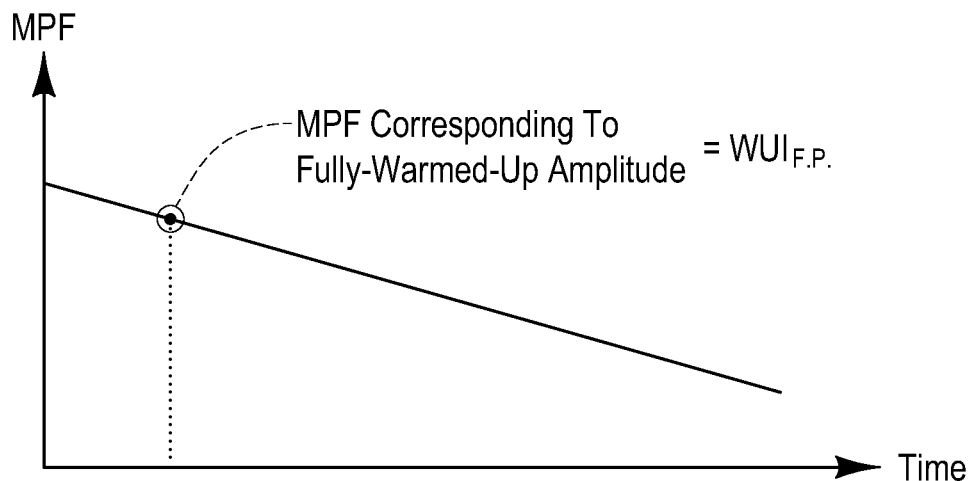
FIG. 7B is a depiction of the MPF vs. time graph where the point corresponding to the indicator shown in FIG. 7A is noted.
Figure 7C:
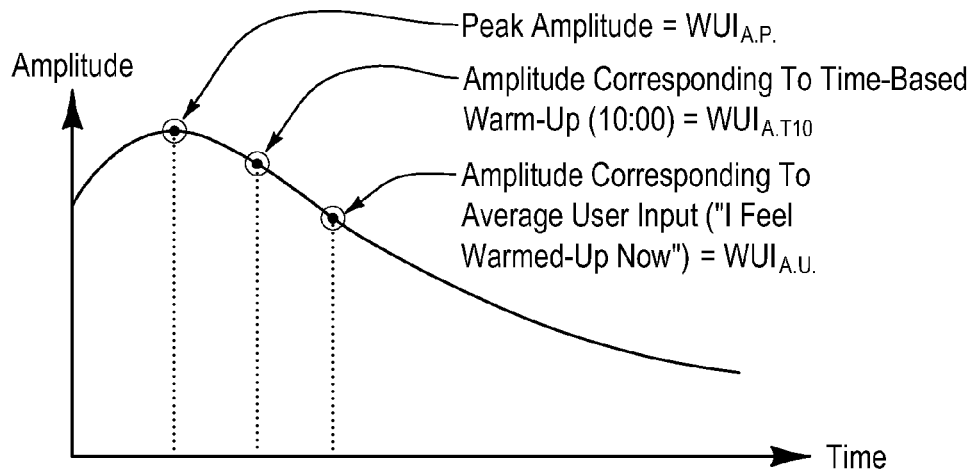
FIG. 7C is a depiction of the amplitude vs. time graph where the first warm-up indicator is noted, as well as the amplitude corresponding to a time based warm-up indicator and average subject input, both being based on a related average dataset.
Figure 7D:
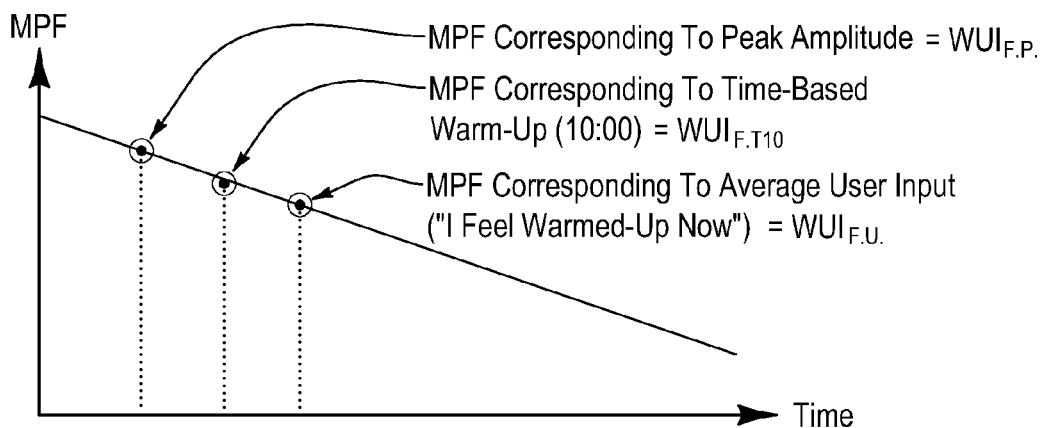
FIG. 7D is a depiction of the MPF vs. time graph where the points corresponding to the indicators shown in FIG. 7C are noted.

The WUI is derived from the method to develop CMOI. Thus, there are two general categories for determining the WUI: amplitude-based WUI, and frequency-based WUI. Like the CMOI method, first, a calibration run is performed by the new subject, and the corresponding data recorded. Then, the maximum amplitude of the resulting amplitude vs. time curve can be used as a time corresponding to a first point of being warmed up as shown in FIG. 7A. The corresponding MPF associated with the time of the max amplitude can also be used as shown in FIG. 7B. Alternatively, as shown in FIGS. 7C and 7D, a database can be referenced through which some number of (e.g., at least 35) data subsets are analyzed, providing different available methods for establishing whether the subject is warmed up. The subjects in the database associated with subsets used can have similar characteristics to the new subject such as physical characteristics, similarities in recorded data or secondary metrics such as MFOI, or the like. When the dataset is created, a number of reference points are recorded for each type of data: the high-point amplitude and corresponding MPF, the amplitude corresponding to a time-based warm-up that is known to be effective based on the database results, for example, 10 minutes, and corresponding MPF for that time is a second warm-up point. In addition, the new subject can also reference the database referencing instead a subject-input experience marker where the subject's in the database feel warmed up and a corresponding time indicating a third warm-up point. Likewise, the subject can find the corresponding MPF associated with that subject-input experience time marker. In this way, an inexperienced subject can benefit from different available methods for establishing whether they are warmed up sufficiently.

Two general categories are described herein: amplitude-based WUI, and frequency-based WUI. In addition to these methods as discussed, the present invention can include a "work done" WUI, which simply sums up the amplitudes over time (e.g., the area under the graph, or integrated signal). The work done can be a simple sum of the RMS sEMG, or it can be FBAAR, or TBAAR (time-based amplitude adjusted). A given target warm-up value based on work done can be calculated the first time based on a database reference for users of similar age, height, weight, or the like. Subsequently, users can also establish time markers that set a work-done goal for the warm-up based on how they are feeling. Note that this is also related to the "Muscle Work Estimation Index."

Figure 7E:
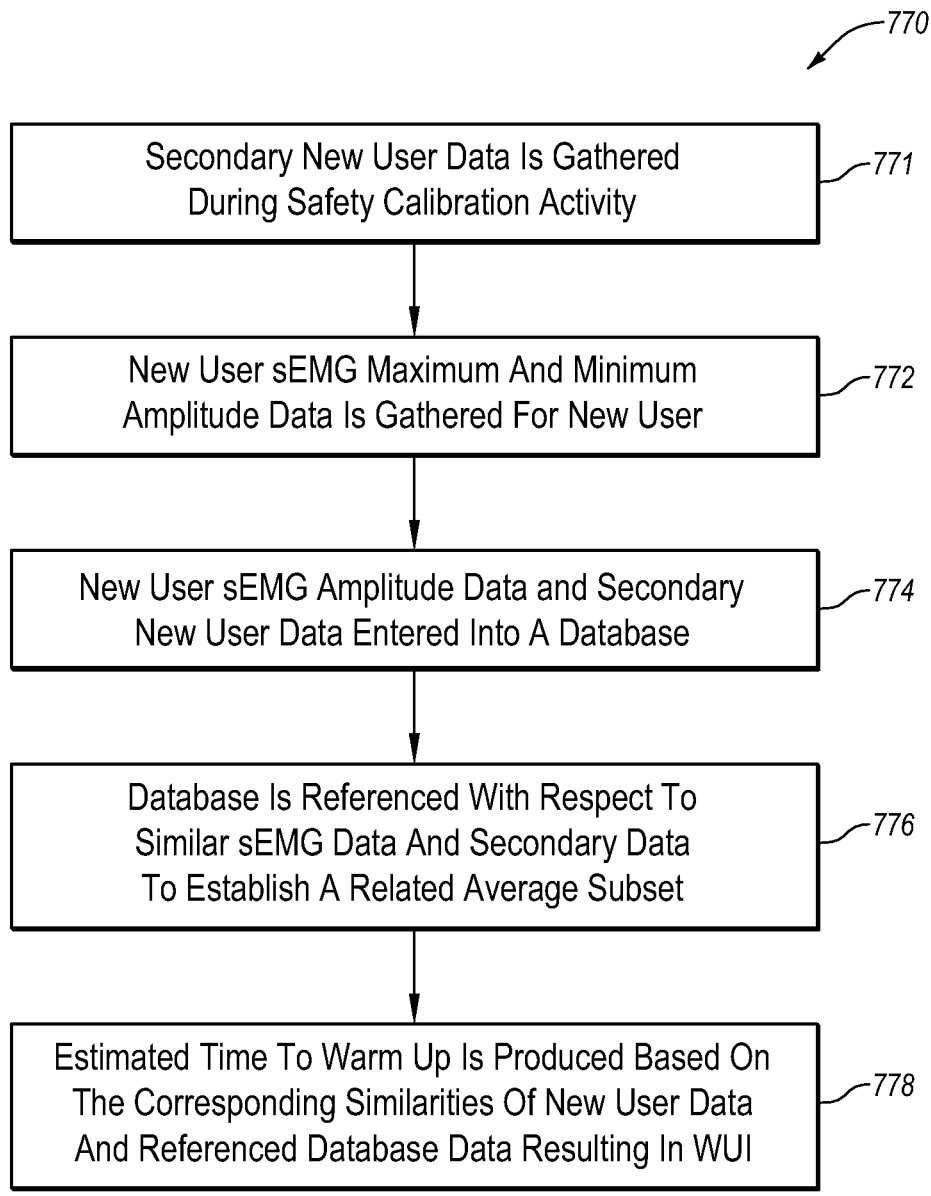
FIG. 7E is a depiction of the subject-amplitude method of determining a new subject warm-up indicator based on new subject data and a related average dataset.

FIG. 7E depicts the method 770 of producing a new subject amplitude-based WUI. First, new subject secondary data is gathered during safety calibration activity (block 771). Second, new subject sEMG data is gathered for the new subject (block 772). Third, new subject sEMG amplitude data and secondary new subject data entered into a database (block 774). Fourth, the database is queried with respect to similar sEMG and secondary data to establish a related average dataset (block 776). Fifth, an estimated time to warm up is determined based on the subset's average time to warm up (block 778). The WUI conversion factor is determined by observing the relationship to the subject data and the average related dataset. Similar to other methods aforementioned, a WUI conversion factor can aid in estimating a warm-up time for a subject engaged in various activities.

Figure 7F:
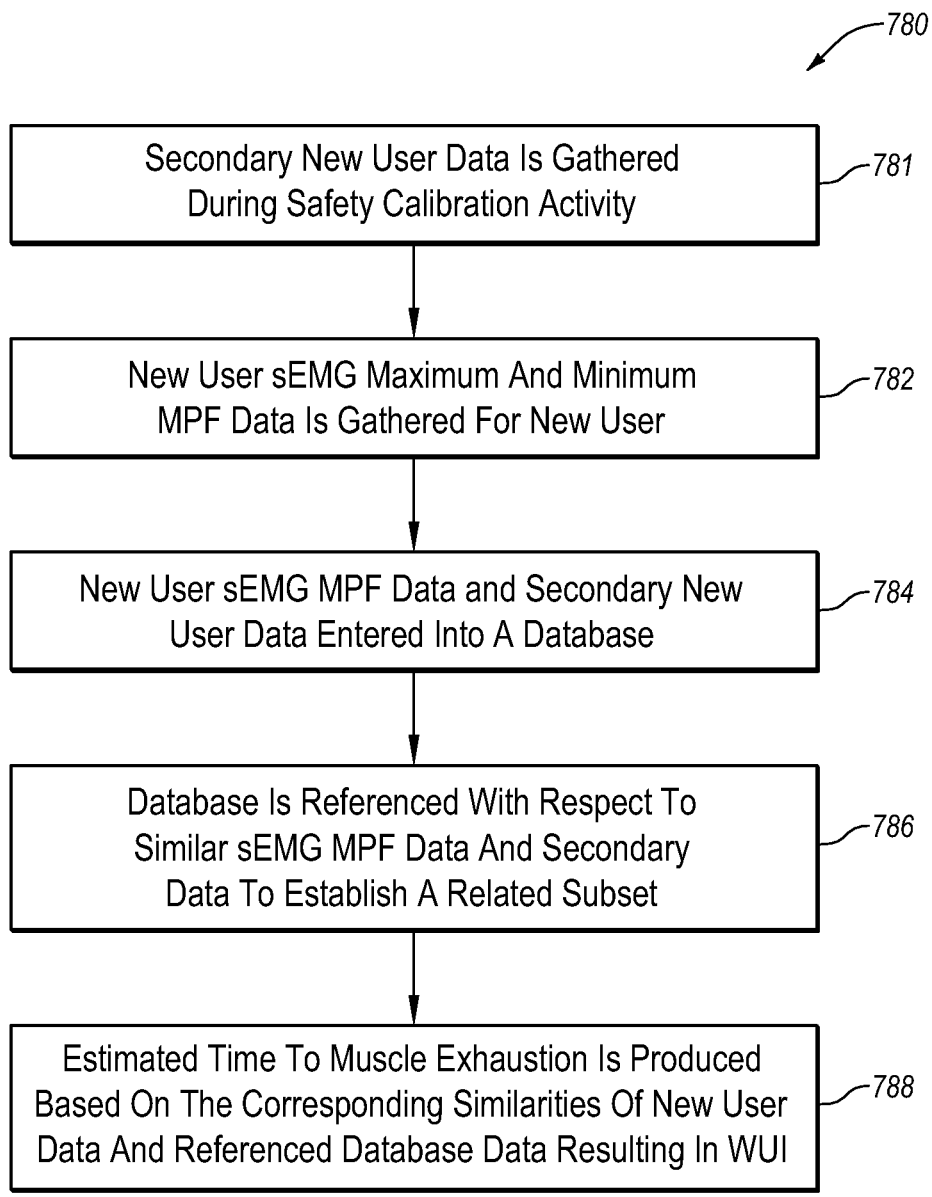
FIG. 7F is a depiction of the subject-frequency method of determining a new subject warm-up indicator based on new subject data and a related average dataset.

FIG. 7F depicts a similar method 780 of producing a new subject estimate for WUI based on a frequency reading. First, new subject secondary data is gathered during safety calibration activity (block 781). Second, new subject sEMG data is gathered for the new subject (block 782). Third, new subject sEMG frequency data and secondary new subject data entered into a database (block 784). Fourth, the database is queried with respect to similar sEMG and secondary data to establish a related subset (block 786. Fifth, an estimated time to warm up is determined based on the subset's average time to warm up (block 788). Similar to the amplitude based WUI, the frequency based WUI conversion factor is determined by observing the relationship to the subject data and the average related dataset. Similar to other methods aforementioned, a WUI conversion factor can aid in estimating a warm-up time for a subject engaged in various activities.

Although two different methods are presented based on different data measurements, either method 770 or method 780 can be used to establish the WUI based on either related average subject data or related average subject direct input.

Impulsive Muscle Overuse Index (IMOI), Pseudo MVC (PMVC)

Figure 8A:
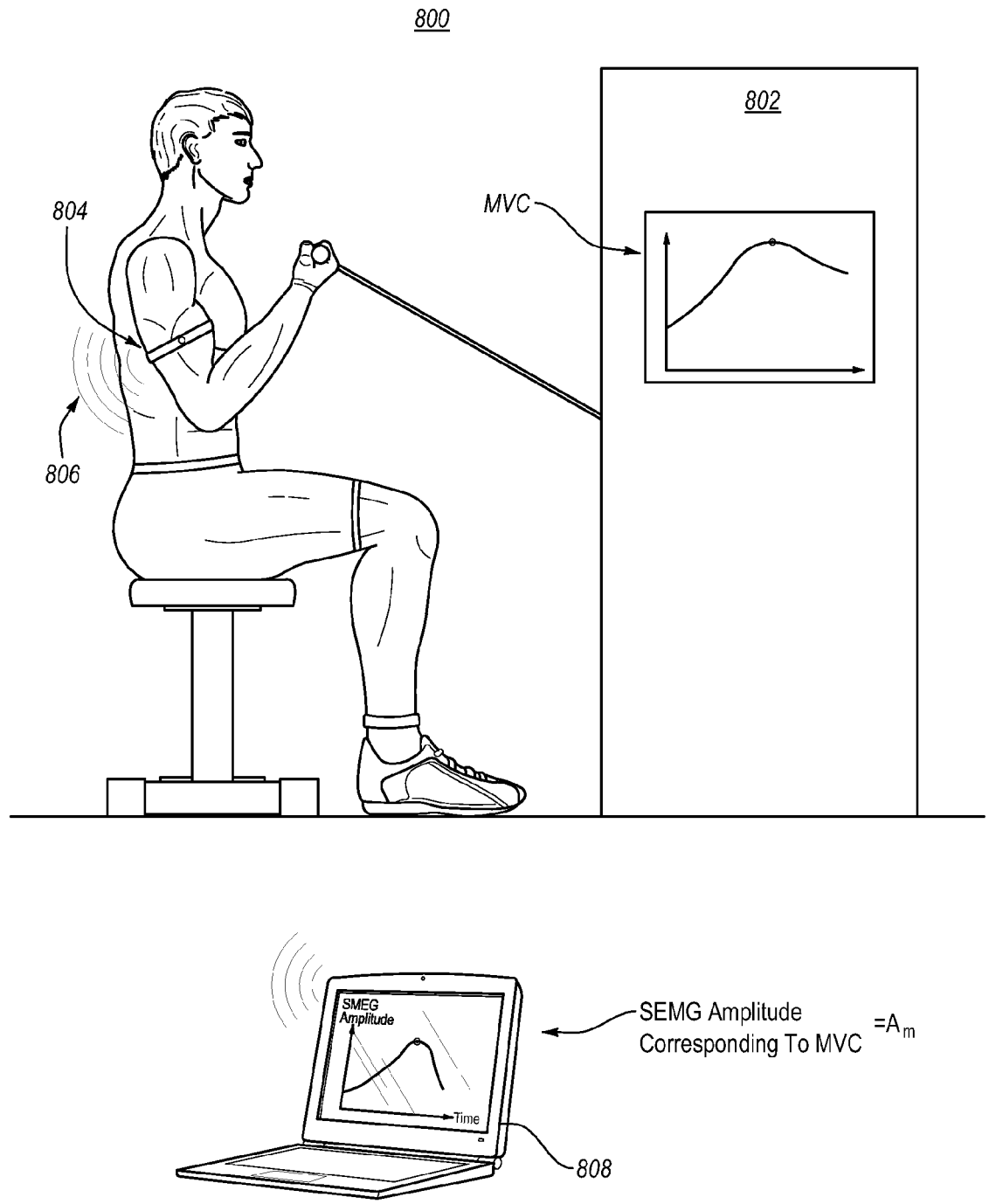
FIG. 8A is a depiction of the current state of the art for measuring maximum voluntary control MVC in a controlled environment and a part of the combined database used to determine the impulsive muscle overuse index (IMOI) conversion factor.

One important consideration when analyzing the amplitude of muscle sEMG signals in the context of athletics is whether the muscle being activated is within a reasonable safety range in terms of how much the muscle is being exerted with respect to its maximum voluntary contraction. Maximum voluntary contraction (MVC) is an established metric that describes the maximum amount of force that a muscle can exert during voluntary isometric contraction, as shown in FIG. 8A. Although FIG. 8A shows one embodiment of a method 800 of obtaining a MVC reading as shown with wireless sensors 804 (e.g., sEMG sensor) that send the sEMG data 806 wirelessly to a computing device 808, it is contemplated by this invention that readings can be taken wirelessly, wired, or otherwise. The method 800 can be implemented during any type of muscle activity, such as weightlifting with a weight machine 802 as illustrated. "Impulsive overuse" defines a safety threshold in relation to the instantaneous force generated by a single muscle contraction. This threshold is typically established by means of calculation of the MVC of an individual. It is known that operating above MVC force levels is dangerous. Excessive muscular contraction force can result in muscle injury, tendon injury, etc. Because of this known danger, the IMOI is proposed as a metric to aid athletes.

Like other metrics aforementioned, IMOI is determined through IMOI protocol by selecting the IMOI protocol. IMOI requires an initial calibration where the user engages in an activity under a semi-controlled environment. As data is gathered, the IMOI protocol will configure data relevant to the IMOI metric such as pseudo MVC (PMVC) explained in detail below. IMOI is determined based on the association of PMVC with known MVC data to create a related average dataset. The IMOI protocol determines a safety force threshold on the basis of the related average dataset.

Figure 8B:
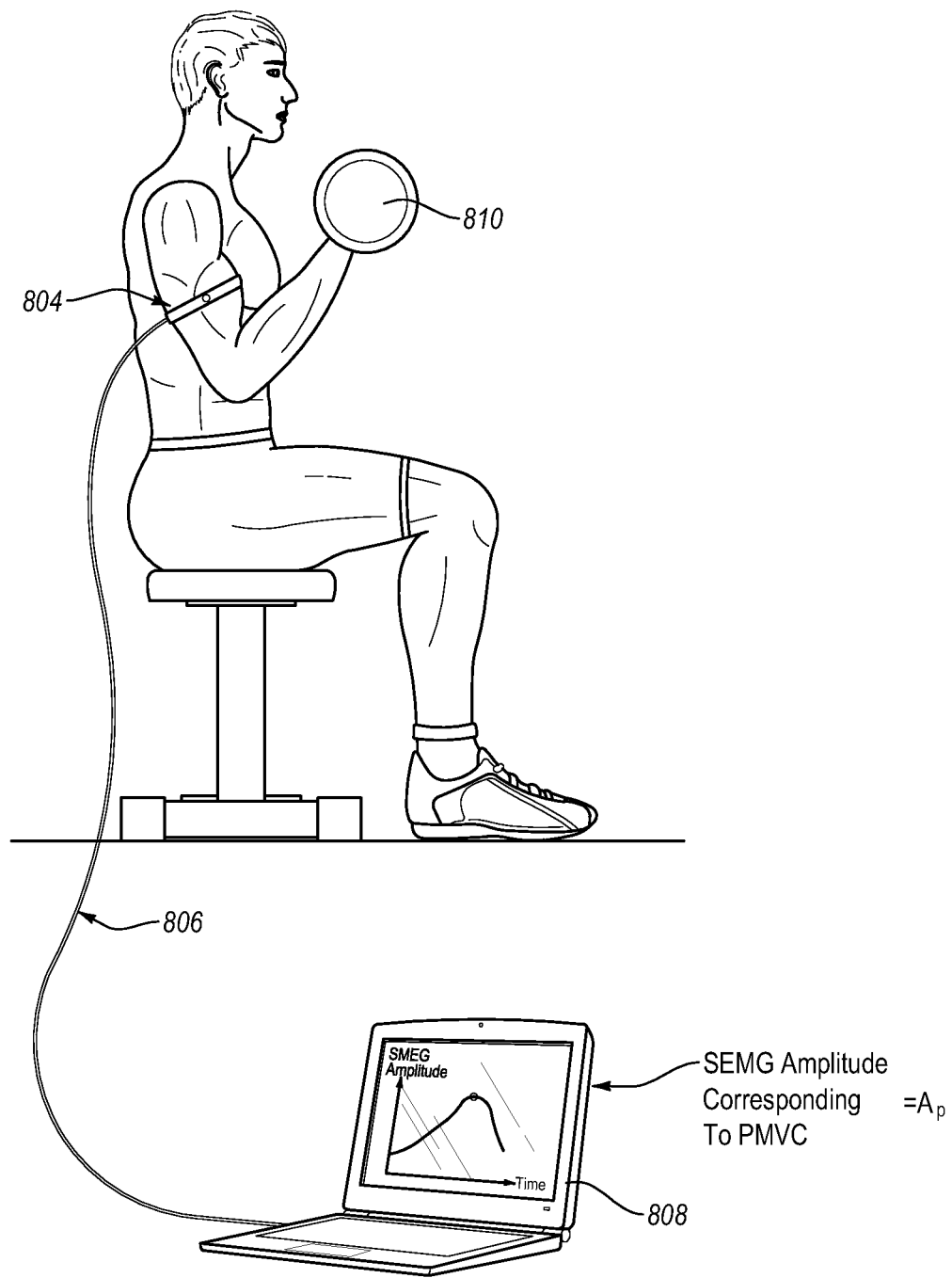
FIG. 8B is a depiction of the system data-gathering pseudo maximum voluntary control (PMVC) measurement in a semi-controlled environment.

In order to obtain useful information, a database is needed which correlates MVC to two metrics. The first metric is called "Pseudo MVC" or PMVC, which like MVC is a metric describing force. The second metric is rectified sEMG, or sEMG amplitude data, which is measured at different force levels. This can include both PMVC and MVC. In contrast to MVC, PMVC is calculated by way of isometric activities performed in semi-controlled environmental conditions such as is shown in FIG. 8B. FIG. 8B shows a subject having a sensor 804 that provides sEMG 806 to a computing device 808 while the subject lifts free-weights 810. Whereas an MVC reading uses isometric activities performed in completely controlled conditions such the MVC reading depicted in FIG. 8A, PMVC is a method for taking readings in semi-controlled environments. For instance, if the weight of a subject is known, and the subject stands on "tip toes" for a time, then the force on each gastrocnemius muscle can be estimated. This is an oversimplified example of a PMVC activity. There are a number of different kinds of isometric activities which subjects can easily and quickly perform which generate estimated force values. During each PMVC and MVC activity in the database, the sEMG amplitude is recorded.

Figure 8C:
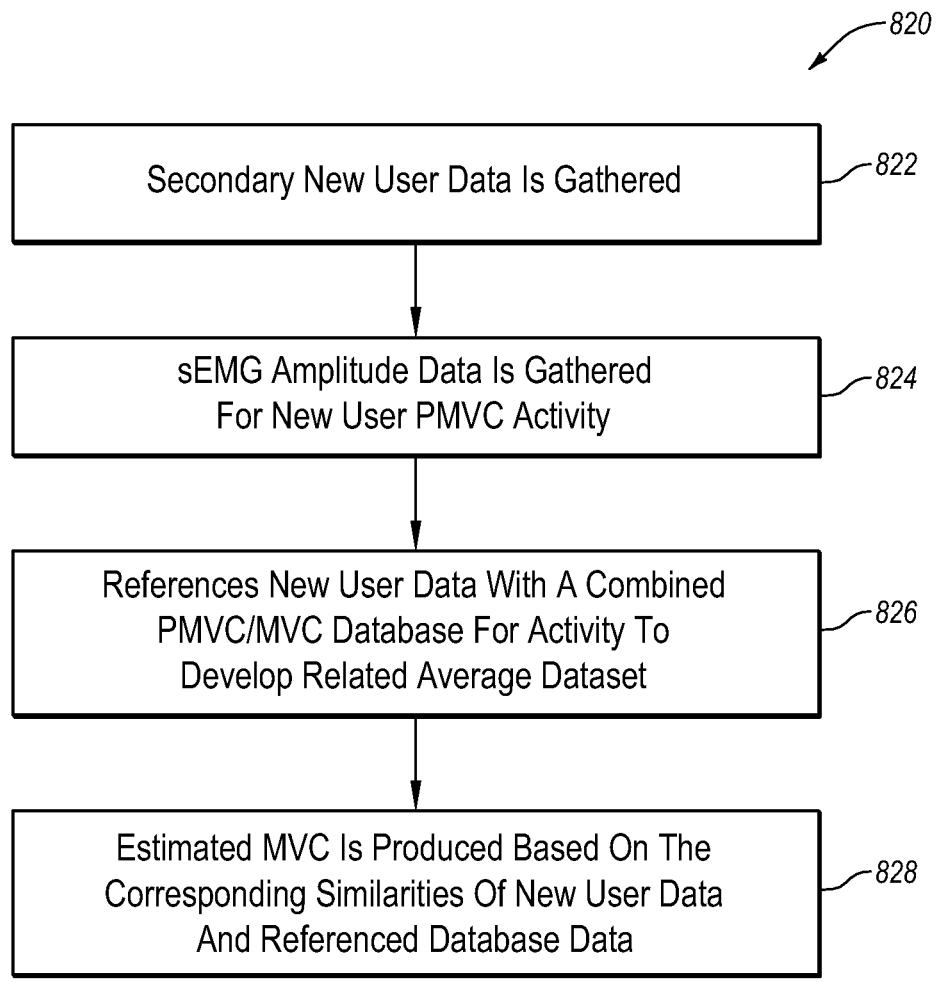
FIG. 8C is a depiction of the method for producing a new subject IMOI, or an MVC estimate, using the PMVC.

A method 820 for determining PMVC is depicted in FIG. 8C. First, secondary new subject data is gathered (block 822). Second, the sEMG amplitude data is gathered for the new subject and the PMVC semi-controlled activity (block 824). The first reference database is comprised of many data sets which include "real MVC" performed in a completely controlled environment, as well as a number of separate PMVC values. The sEMG amplitude is measured for both MVC and PMVC. When a new subject (e.g., who is not in the database) performs a PMVC-inducing activity such as in FIG. 8B, the database can be used to correlate the PMVC to MVCs for individuals who have similar physical properties. The third step of the method 820 is to reference the new subject data with a combined PMVC/MVC database to develop a related average dataset (block 826). After the related average dataset is produced, the next step is to estimate MVC for the semi-controlled PMVC activity based on the dataset (block 828). Direct mathematical conversion between PMVC and MVC (with a calculated and disclosed error range) is also possible, without consulting the database using a PMVC/MVC conversion factor. A PMVC/MVC conversion factor is determined by modeling or approximating the relationships found within the database between PMVC and MVC. Either way, with or without direct database access, when a new subject performs a PMVC activity, and their sEMG amplitude is recorded, the corresponding conversion factor between PMVC sEMG amplitude and MVC sEMG amplitude is used to convert the new subject's PMVC sEMG amplitude into estimated MVC sEMG amplitude. This estimated MVC sEMG amplitude which is based on PMVC sEMG levels, database comparison, and analysis produces an IMOI. IMOI is the sEMG amplitude level which corresponds to an estimated safety threshold due to impulsive or instantaneous overloading or overuse.

Further, if it is experimentally determined that for the sake of mitigation of liability that some percentage of MVC is the practical safety limit (for instance, 70% MVC) during any given activity, this can be calculated in the same manner as specified above. The method for calculating a new threshold based on a more conservative approach is outlined in FIG. 8C described above.

In summary, IMOI are calculated by way of the following algorithmic process: a) a new subject decides they would like to know their IMOI for a given muscle group; b) the subject must enter information about themselves such as height, weight, age, or the like into the system; c) the subject selects an appropriate PMVC activity, and performs the activity while recording sEMG amplitude; d) the database is called, and the subset corresponding to age, height, specific muscle being measured, PMVC activity type, etc. is referenced; e) for that database subset, the average sEMG amplitude observed during MVC is calculated; f) for that same database subset, the average sEMG amplitude for the PMVC activity type, and for that specific muscle, is calculated; and g) the conversion factor (CF) between PMVC and MVC for that subset is calculated by Equation 11.

$$CF = MVC/PMVC \quad \text{Equation 11}$$

It should be noted that CR is the conversion ratio calculated by Equation 12.

$$CR = A_{m(average)}/A_{p(average)} \quad \text{Equation 12}$$

The distinction here is between a ratio of force (CF) and a ratio of two amplitudes (CR).

Thus, the algorithm can include: h) the sEMG amplitude measured by the new subject (from step "c") is multiplied by the conversion factor CF (step "g"). Assuming that the activity coordinators are comfortable with 100% MVC being the practical safety limit, this calculated value is the IMOI (e.g., measured in microvolts). This is the safety threshold. An embodiment of this metric can be used in a real time feedback device that notifies the subject when he/she is approaching the threshold.

Assuming that the activity coordinators are comfortable with some fixed percentage of MVC being the practical safety limit of an activity (for instance, 70% MVC), then the above-calculated IMOI value in step "h" is multiplied by the appropriate percentage (e.g., in this case, 0.7). Then, the resulting value (e.g., in microvolts) is the IMOI.

It may be advantageous to adjust for fatigue. The above assumes that all measurements are being made with equally fatigued muscles. It is known that when muscles are fatigued through use over time, the observed amplitude for a given activity will change.

Muscular Work Estimation Index (MWEI)

Figure 9A:
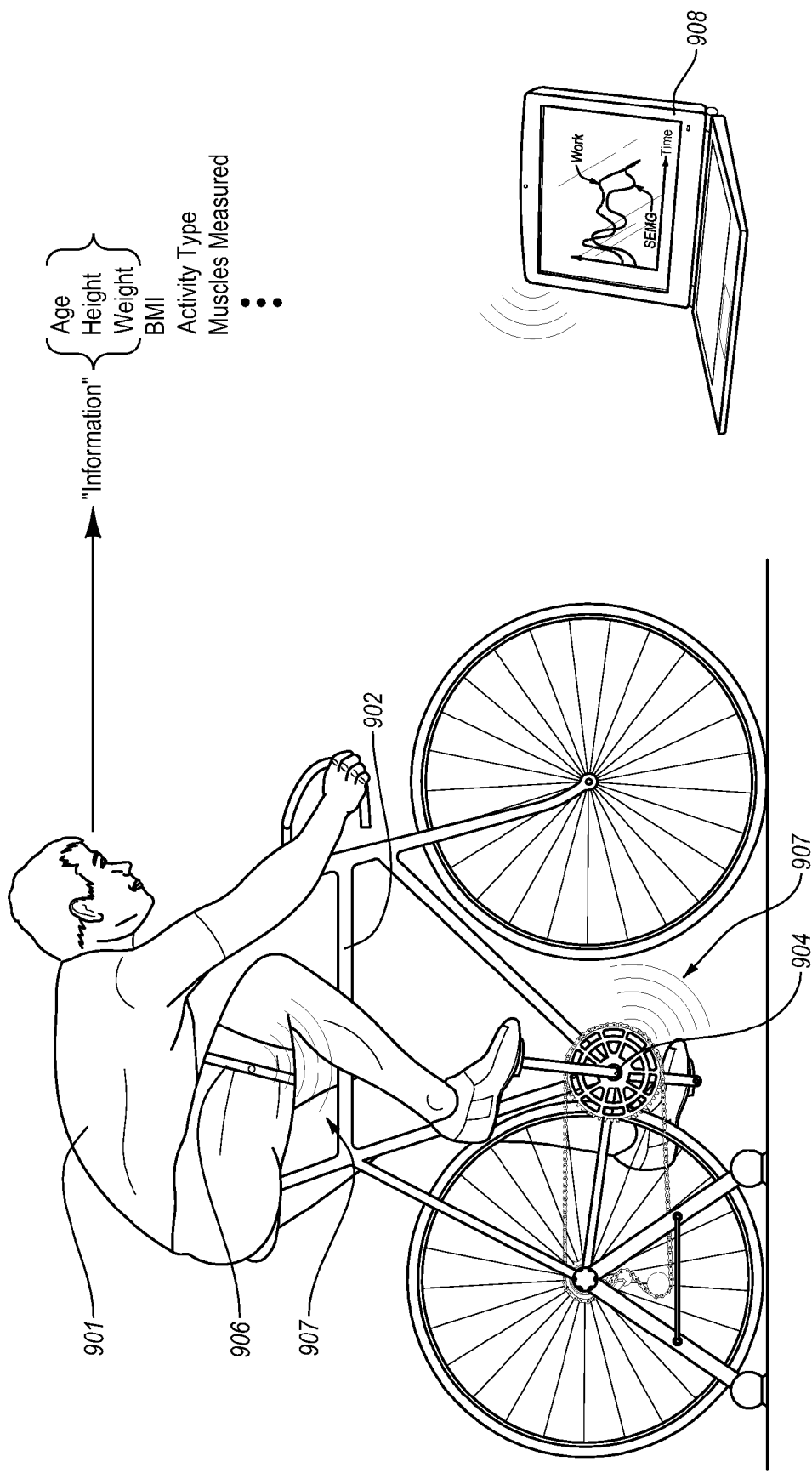
FIG. 9A is a depiction of a system for measuring and estimating work for various activities using the Muscle Work Estimation Index (MWEI) conversion factor.

The work done during one or more isotonic contractions can be measured by an ergometer. In the past, this has been the only way for a subject to track or monitor the amount of work that they were doing during any given exercise. A new method of measuring work and receiving feedback can be performed by using work index that measures data provided by a subject engaged in an activity as in FIG. 9A. FIG. 9A illustrates a subject riding a bike 902 that has a work sensor 904 (e.g., work ergometer) while wearing a leg sensor 906. The sensors 904, 906 wirelessly communicate data 907 to a computing device 908. In order to calculate the muscular work estimation index (MWEI) and an MWEI conversion factor, a database is needed to correlate work done with the integral of a rectified sEMG graph (e.g., area under the curve of a rectified sEMG graph). The database can be built with subject information.

Like other metrics aforementioned, MWEI is determined through MWEI protocol by selecting the MWEI protocol. MWEI requires an initial calibration where the user engages in an activity under a semi-controlled environment. As data is gathered, the MWEI protocol will configure data relevant to the MWEI metric such as integrated sEMG amplitude and work output. MWEI is determined based on the association of sEMG amplitude data with work output data to create a related average dataset conversion factor. The MWEI protocol thus allows sEMG data to be converted to work done.

Figure 9B:
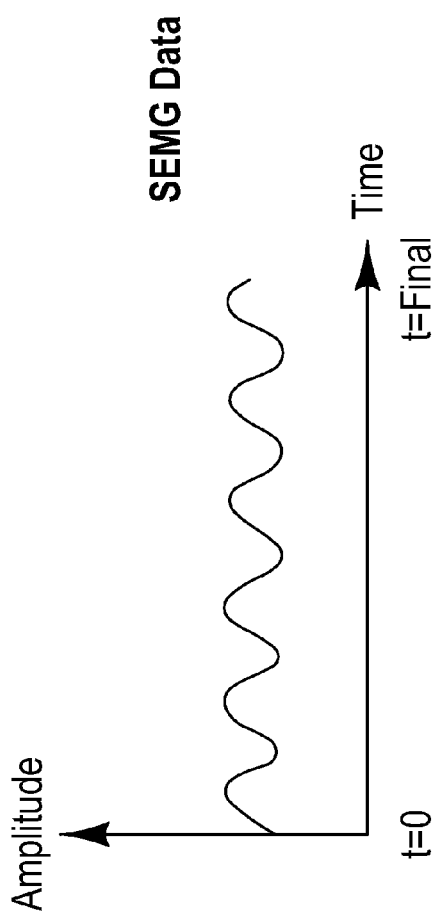
FIG. 9B is a depiction of the amplitude vs. time graph of the data gathered for the new subject activity to be used in creating an MWEI conversion factor.
Figure 9C:
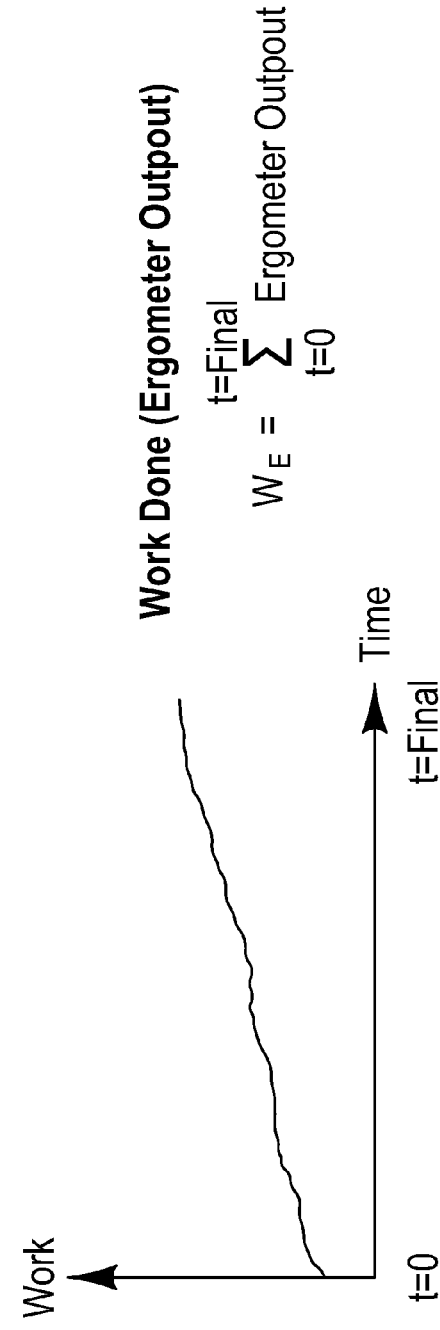
FIG. 9C is a depiction of the work vs. time graph of the data gathered for the new subject activity to be used in creating an MWEI conversion factor.
Figure 9D:
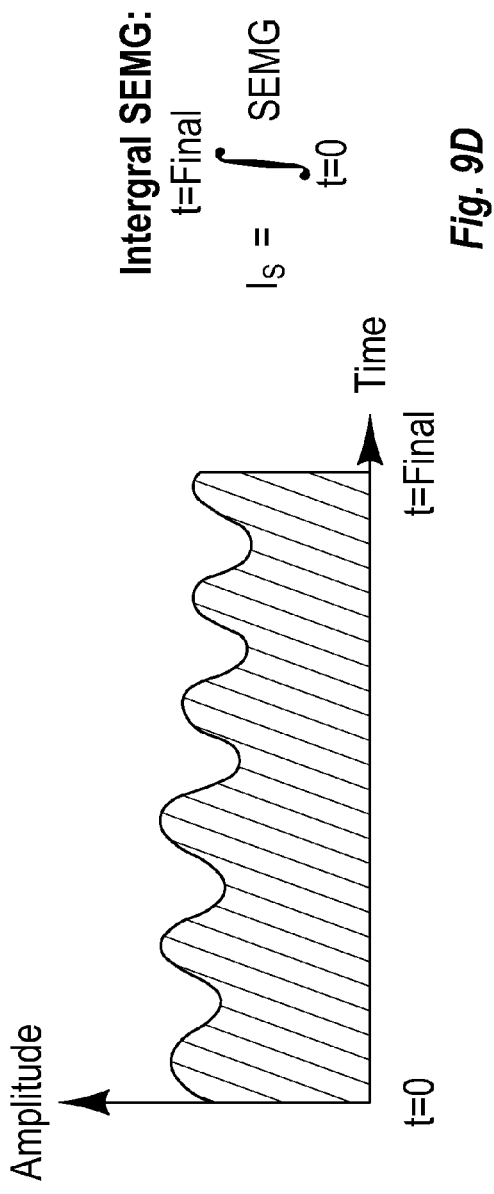
FIG. 9D is a depiction of an integral of the amplitude vs. time graph for a related average dataset, where the area under the curve is useful in calculating the MWEI conversion factor for a given activity.

In order to build a database, each person whose data is entered into the database discloses secondary subject data such as age, height, weight, and a number of other physiological measurements which they either already know or which can be easily determined experimentally (e.g., such as measuring body mass index, BMI). Then, the subjects perform specified activities in a semi-controlled environment (e.g., rowing machine, stationary bike, treadmill, resistance training machine, or the like). In FIG. 9B sEMG amplitude is being measured the entire time that subjects are performing the activity. As depicted in FIG. 9C work done by the activity is also being recorded. Every incoming data point includes multiple dimensions, including sEMG amplitude for associated times, integrated sEMG from t=0 until t=final shown in FIG. 9D, and work done from t=0 until t=final as measured by the ergometer associated with the machine, are all recorded.

Integrated sEMG is shown by Equation 13.

$$\int_{t=0}^{t=final} sEMG \quad \text{Equation 13}$$

Work done is shown by Equation 14.

$$\Sigma_{t=0}^{t=final} \text{ergometer output} \quad \text{Equation 14}$$

Then, the conversion factor between integrated sEMG and work done is calculated by dividing the calculated work done (e.g., from t=0 until t=final) by the area under the curve of the rectified sEMG graph (e.g., from t=0 until t=final) shown by 15.

$$CF = \left( \frac{\sum_{t=0}^{t=final} \text{ergometer output}}{\int_{t=0}^{t=final} sEMG} \right) \quad \text{Equation 15}$$

Figure 9E:
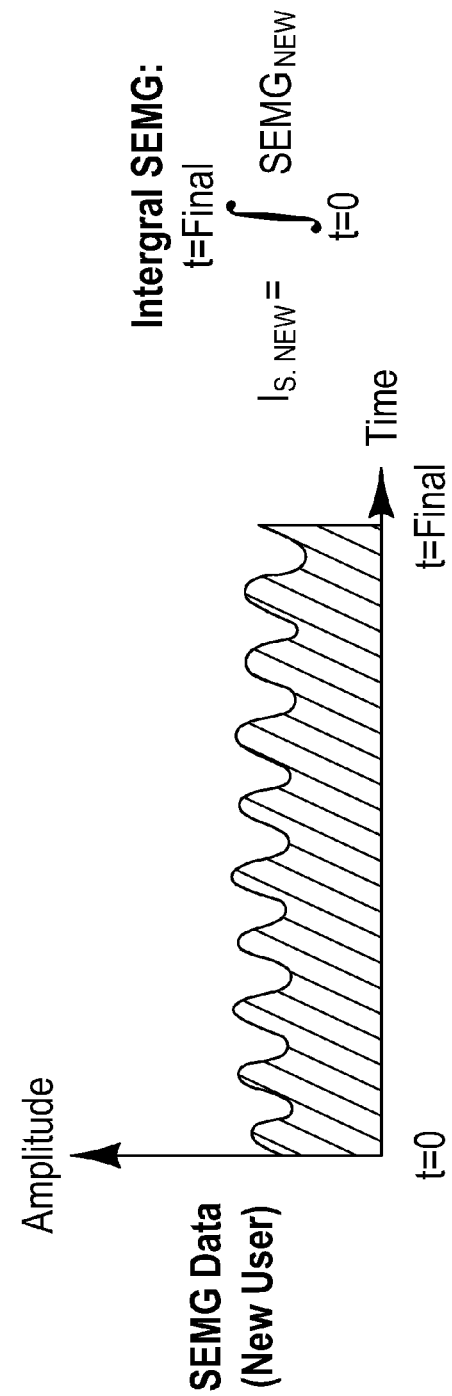
FIG. 9E is a depiction of an integral of the amplitude vs. time graph of new subject data, where the area under the curve is useful in calculating the MWEI conversion factor for any given activity.

When a new subject performs an activity, such as in FIG. 9E, the new subject's integrated sEMG (e.g., from t=0 until t=present) is calculated. Then, the new subject's integrated sEMG is multiplied by the average conversion factor $CF_{average}$ associated with the data subset's corresponding to the new subject's data, yielding an estimated value describing the amount of work that was done by that particular muscle of the individual performing that particular activity. This value is the MWEI.

Thus, MWEI is determined by Equation 16.

$$MWEI = sEMG_{new\ subject} * CF_{average} \quad \text{Equation 16}$$

Skeletal Muscle Calorie Index (SMCI)

Currently, caloric expenditure is estimated by way of measuring an individual's heart rate (HR) and then using that measurement in a very general formula to determine caloric burn. However, calculating caloric expenditure based on heart rate is inherently crude estimation, and as such contains a high likelihood of error/inaccuracy for any given individual.

Each time a muscle contracts, there is an energy cost, as measured in calories. While heart rate is a relatively inexpensive estimation method (e.g., because heart rate monitors have become relatively inexpensive), it lacks accuracy and specificity based on muscle type, activity type, or the like.

A database can be used to provide a more robust estimate of caloric burn. This database can be multidimensional, and can be sorted by muscle, by activity, and by secondary factors such as: age of subject, BMI of subject, height of subject, as well as a number of other factors as mentioned in databases required for other methods/metrics listed herein. The function of this database is to correlate the caloric expenditure of certain activities with the area under the curve of the rectified sEMG graph recorded during those activities. The database can be created by performing activities that are "simple": a single muscle performing a single action, while recording the caloric expenditure of that single action as well as the area under the rectified sEMG graph for that single action. The protocol can use the most accurate measures of caloric expenditure available. Namely, established methods can be used, such as in a controlled environment that measures the change in temperature of the subject to gauge caloric expenditure. There are several other methods available for this, none of which are central to the SMCI. Regardless of method, when a known caloric cost is associated with the area under a rectified sEMG graph, on a muscle-by-muscle basis, for individuals with similar physical characteristics, this relationship can be harnessed and conversion factors can be created.

Like other metrics aforementioned, SMCI is determined through SMCI protocol by selecting the SMCI protocol.

SMCI requires an initial calibration where the user engages in an activity. As data is gathered, the SMCI protocol will configure data relevant to the SMCI metric such as integrated sEMG amplitude and caloric expenditure. SMCI is determined based on the association of sEMG amplitude data with caloric expenditure data to create a related average dataset conversion factor associating sEMG data with an average caloric burn. The SMCI protocol thus allows sEMG data to be converted to caloric expenditure. The SMCI can be used for a single muscle, or multiple muscle groups.

Once the data has been associated with a caloric burn, a conversion factor is created, including some additional steps. This is done by first creating a conversion factor associating the total number of calories burned with the area under the subject's rectified sEMG data curve for that particular muscle, represented by Equation 17:

$$CF = \left( \frac{\text{Total Calories Burned}}{\int_{t=0}^{t=final} sEMG} \right) \quad \text{Equation 17}$$

For multiple muscles or multiple muscle groups associated with the same activity, the conversion factor can be modified by Equation 18:

$$CF = \left( \frac{\text{Total Calories Burned}}{\Sigma \int_{t=0}^{t=final} sEMG} \right) \quad \text{Equation 18}$$

When a new subject performs an activity while live rectified sEMG data is being recorded, the database is referenced, and the area under the subject's rectified sEMG data curve for that particular muscle, or multiple muscles/muscle groups be correlated with an associated caloric cost. Once the new subject's integral rectified of sEMG data has been converted to an associated caloric burn, the new subject's SMCI can be calculated.

SMCI is calculated by gathering a subset from the database based on data related to the new subject's data, producing a subset of a number of (e.g., at least 35) subjects in the subset, and a conversion factor for each. An average conversion factor is calculated by Equation 19:

$$CF_{subset\ average} = \left( \frac{\sum_{n=1}^{n=total} CFn}{total} \right) \quad \text{Equation 19}$$

Finally, the new subject's integral rectified sEMG data is converted to the new subject's SMCI by Equation 20:

$$SMCI = (\Sigma \int sEMGnew) \times (CF_{related\ average\ dataset}) \quad \text{Equation 20}$$

Thus, a SMCI can be tailored for the subject and for the activity. For any given activity, there are certain muscles which are primary contributors to the caloric cost of the activity. For instance, running and bicycling result in caloric expenditure that is primarily due to core muscle activation and lower extremity activation (e.g., gluteus muscles, leg muscles). Monitoring the sEMG output of these muscles will produce a more tailored estimate of caloric expenditure which uses the electrical output of the muscles to estimate caloric burn, instead of status-quo Heart Rate-only methods.

Cardio-Skeletal Muscle Calorie Index (CMCI)

The cardio-skeletal muscle calorie index (CMCI) is similar to the Skeletal Muscle Calorie Index. The major differentiating factor is that two databases are utilized, however, and they may be combined into a single database. Essentially, this is a combination index which utilizes previously established heart rate-only methods of caloric expenditure, and also estimates of calories burned based on the more accurate skeletal muscle calorie index as well.

Like other metrics aforementioned, CMCI is determined through CMCI protocol by selecting the CMCI protocol. CMCI requires an initial calibration where the user engages in an activity. As data is gathered, the CMCI protocol will configure data relevant to the CMCI metric such as integrated sEMG amplitude and heart rate (HR) data. CMCI is determined based on the association of sEMG amplitude data with HR data and a known HR caloric expenditure database to create a related average dataset conversion factor associating sEMG data with an average caloric expediture. The CMCI protocol thus allows sEMG data to be converted to caloric expenditure. The CMCI can optionally be calculated with weights on sEMG amplitude or HR caloric expenditure as determined to appropriate.

One description of a method to determine a CMCI would be as follows. An individual performs a muscle activity, and the HR and rectified sEMG data are both recorded for the duration of the activity. A previously established database determines the relationship between HR and calorie burn can be obtained or determined, producing an estimate of calories burned (CHR). The second database, such as the SMCI database expressed above, empirically establishes the conversion factor by the relationship between rectified sEMG data and calories burned using the area under the rectified sEMG curve, and produces a second estimate of calories burned (CRS). The CMCI is then calculated by Equation 21.

$$CMCI\_1 = (0.5*CHR) + (0.5*CRS) \quad \text{Equation 21}$$

This equation expresses equal weights on each database, however, different weights can be assigned to either the CHR value or the CRS value depending on preference.

Muscle Activation Symmetry Index (MASI) and Normalized Muscle Activation Symmetry Index (NMASI)

Muscle activation refers to rectified sEMG amplitude. Symmetry refers to left-side and/or right-side muscles, such as the left quadriceps femoris and the right quadriceps femoris. "Normalized" refers to a database which describes normal variation in symmetry found in sEMG measurements during particular activities derived from a series of studies using statistically significant numbers of subjects. Symmetry in this context can refer to a logically grouped pair of muscles.

Instantaneous left-side amplitude (ILSA) is the rectified sEMG amplitude of a muscle on the left side of the body. Instantaneous right-side amplitude (IRSA) is the rectified sEMG amplitude of a muscle on the right side of the body. Thus, MASI is defined by Equation 22.

$$MASI = IRSA - ILSA \quad \text{Equation 22}$$

By setting a precedent that MASI is always calculated by subtracting the right side from the left side, the sign of the resulting MASI (+/−) becomes significant, and can quickly tell the subject which side of their body is exhibiting greater activation potentials, and what that difference is between those potentials.

Like other metrics aforementioned, MASI is determined through MASI protocol by selecting the MASI protocol. MASI requires an initial calibration where the user engages in an activity. As data is gathered, the MASI protocol will configure data relevant to the MASI metric such as rectified sEMG amplitude for the right and left side of a symmetrical muscle group. MASI is the difference between the right side and left side amplitude.

The difference index MASI, when compared to the normalized difference index NMASI, can help describe the manner an individual performs a certain type of physical activity. For example, if it is known that for 1000 subjects who have had the rectified sEMG amplitude of their left and right quadriceps femoris measured while swimming 100 meters, the average NMASI can be shown to be 50 microvolts, then this normalized difference index can be used when a new subject decides to swim 100 meters while measuring their sEMG amplitude. If the new subject's MASI is 30 microvolts, then they are within a normal difference index range for that muscle group, that activity, and that particular subset of subjects which correlate to the new subject's physical characteristics. In other words, if MASI≤NMASI, the difference index is normal. If MASI>NMASI, difference index is not normal.

Lack of normality can indicate different situations. It could indicate a recruitment pattern (e.g., learned behavior) that is asymmetrical. If that is the case, then the individual would benefit from training and re-education. It could indicate that the subject has an injury on one side of their body, and is favoring the other side. If that is the case, then the subject should probably not yet be performing that activity (e.g., possibly because a subject is not fully recovered from injury yet). It could also indicate that one side of the subject's body is significantly stronger than the other side. If that is the case, then the subject should strengthen the side of their body that is weaker. Regardless, MASI versus NMASI is a valuable tool for individuals who perform physical activities that require equal force from both sides of their bodies.

It shall be appreciated that these comparisons can be done not only for instantaneous measurements but also for measurements taken over a period of time. This is accomplished by either taking the integral of the MASI readings for each symmetrical side of a muscle or muscle group, or by taking the average. The integral of MASI is defined by Equation 23.

$$MASI_{integral} = \int_{t=0}^{t=n} A:\text{right} - \int_{t=0}^{t=n} A:\text{left} \quad \text{Equation 23}$$

MASI average is defined by the Equation 24

$$MASI_{average} = A_{R(average)} - A_{L(average)} \quad \text{Equation 24}$$

Muscle Work Difference Index (MWDI) and Normalized Muscle Work Difference Index (NMWDI)

Muscle work difference index (MWDI) and normalized work difference index (NMWDI) are similar to MASI, but they differ from MASI in a few significant ways. The simplest way to clearly define MWDI or its counterpart NMWDI is to describe the difference between MASI and MWDI.

First, MASI only is used to describe left versus right side of the body, as measured only in a single muscle group. In contrast, MWDI may compare the difference between left versus right in a single group, but may also compare one muscle group to another. For instance, right biceps brachii can be compared to right triceps brachii during an isotonic machine bench-press. MWDI may also compare a work difference index for two individuals with the measurement being performed on exactly the same muscle. It may also be a work difference index for the same individual, and the same muscle, but on different days and/or at different times.

Second, MWDI utilizes muscular work estimation index (MWEI) explained above. MWDI is a comparison of work done, not of sEMG amplitude observed. While these are proportional, the difference observed is affected by the conversion factor used to convert between amplitude over time and/or area under the curve to work done. In this sense, since numbers describing work done are always larger than numbers describing instantaneous activation levels (e.g., an extra dimension of time is utilized, as well as the amplitude dimension) it is a more sensitive measurement. Additionally, this measure allows for more comparisons over time and a more complete understanding of how a muscle works.

Like other metrics aforementioned, MWDI is determined through MWDI protocol by selecting the MWDI protocol. The MWDI protocol in turn utilizes the MWEI protocol aforemention. The MWDI protocol determines at least a first value and a second value representing the work done for each muscle or muscle group measured. MWDI is the difference between the first value and the second value. This is useful when compared to past datasets, average datasets of the same user or average datasets for other users. An average dataset comparison is called the NWDI.

Thus, after a first related MWEI data set and a second related MWEI data set are created, the values are subtracted to determine MWDI. If MWDI≤NMWDI, difference index is normal. If MWDI>NMWDI, difference index is not normal.

Slow-Twitch Muscle Indexes (STMI)

The slow-twitch muscle indexes (STMI) are a family of metrics that are extracted from a single calibration activity, not a database. STMI is derived from a method for graphical/analytical filtering (e.g., viewing only slow-twitch fiber activation) as well as a method for quantifying slow-twitch fiber activation in a variety of ways, including maximum amplitude of slow-twitch muscle fiber activation, average amplitude of slow-twitch muscle fiber activation, rate of fatigue of slow-twitch muscle fibers, length of time required before slow-twitch fibers become the primary force behind an activity, and work done by slow-twitch fibers during an activity.

Like other metrics aforementioned, STMI is determined through STMI protocol by selecting the STMI protocol. The STMI protocol gathers sEMG data and then measures the inflection point. The inflection point is determined on the graph of sEMG amplitude versus time or the corresponding MPF versus time. The inflection point represents the point at which fast-twitch muscle fibers become a secondary force to slow-twitch muscle fibers.

Figure 10A:
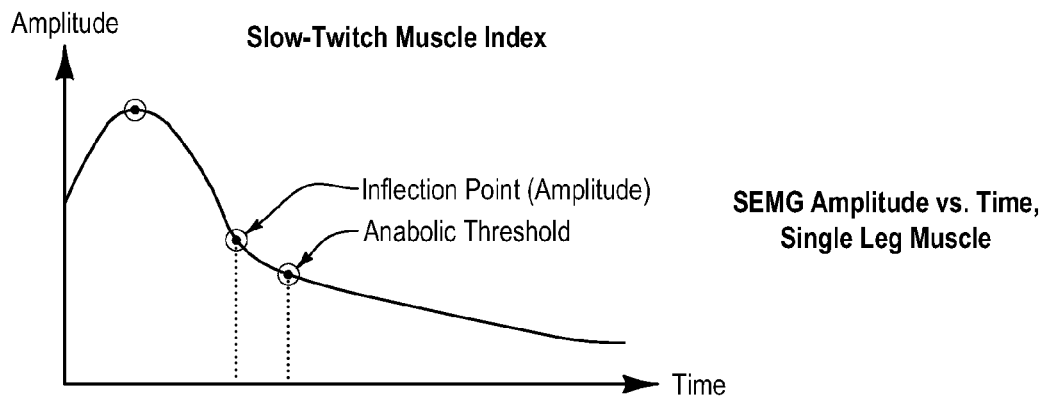
FIG. 10A is a depiction of the sEMG data displayed on an amplitude vs. time graph useful in determining the slow-twitch muscle index (STMI) conversion factor, and the fast-twitch muscle index (FTMI) conversion factor, noting points including an inflection point before which fast-twitch fibers dominate the activity and after which slow-twitch fibers dominate the activity.
Figure 10B:
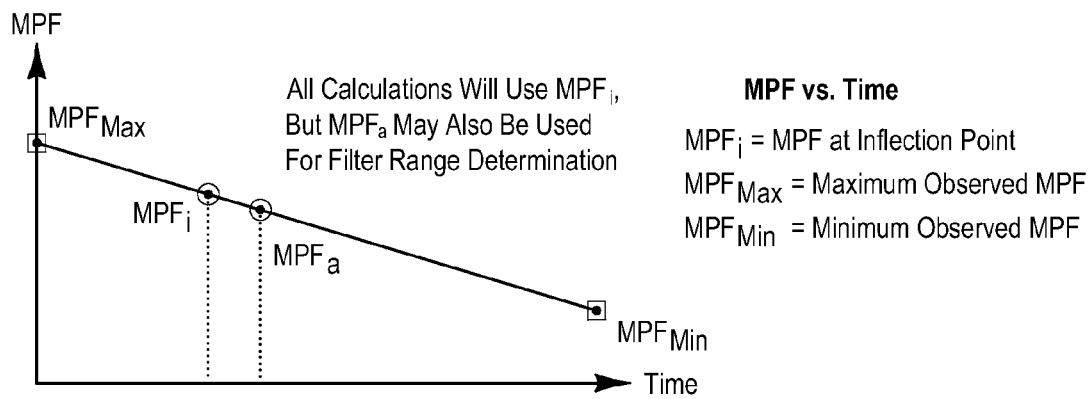
FIG. 10B is a depiction of the MPF vs. time graph noting points from FIG. 10A and their corresponding points on the MPF vs. time graph.

An individual who wishes to determine "how much" and "for how long" their slow-twitch muscle fibers activate during physical activity first applies sensors and/or devices for the measurement of sEMG amplitude and frequency. The individual then performs the activity, which is rate-controlled and exertion-controlled to the greatest extent possible. For example, if a runner wishes to determine their STMI, they might apply sensors, and then run on a treadmill for 30 minutes at 5.5 mph, with a fixed stride rate of 120 heel strikes per minute (hspm). As shown in FIG. 10A, the resultant sEMG amplitude graph is observed, and the inflection point between the initial rate of change decrease and secondary rate of change decrease is marked. In FIG. 10B, the graph of MPF versus time is superimposed on the graph of amplitude versus time, so that at the point of inflection noted, the MPF of that transition point can be likewise determined. Then, a band-pass filter is implemented retroactively on the graph, with the allowed frequency range being equal to or less than the MPF of the transition point. Since initially observed amplitudes and frequencies are due to fast-twitch fiber activation, and these fibers become relatively quickly fatigued, by filtering out the frequencies above the MPF of the transition point, the fast-twitch fibers are eliminated from the observed data.

For example, it has been experimentally observed that during a 30-minute run, initial sEMG amplitudes are significantly higher than later sEMG amplitudes. There are also two distinct drop-off rates. Initially, fast-twitch fibers dominate the observed amplitude signals. After roughly 12 minutes of running, amplitude drops severely, and frequency as decreased as the fast-twitch fibers have fatigued and slow-twitch fibers start to predominate the signal.

The following is an example of how this might manifest: Initial amplitude being 2000 microvolts (average); Initial MPF being 180 Hz; Inflection point time being 12 minutes; Inflection point amplitude being 800 microvolts; Inflection point frequency being 100 Hz; Final amplitude being 100 microvolts; Final MPF being 70 Hz; and/or STMI band-pass filter set-up being 5-100 Hz.

Looking only at Slow-Twitch Muscle Index (STMI), we now can start to calculate the following: Maximum amplitude of slow-twitch muscle fiber activation; Average amplitude of slow-twitch muscle fiber activation; Rate of fatigue of slow-twitch muscle fibers; The length of time required before slow-twitch fibers become the primary force behind an activity; and/or work done by slow-twitch fibers during an activity. The maximum amplitude of slow-twitch muscle fiber activation can include the maximum amplitude being the amplitude of the rectified sEMG graph at the inflection point. The average amplitude of slow-twitch muscle fiber activation can be the average amplitude of the rectified sEMG graph from the inflection point until the end of the session. The rate of fatigue of slow-twitch muscle fibers can be calculated by looking at the slope of a line, or rate of change, which is fit to the graph of MPF versus time, from the point of inflection until the final point, represented by Equation 25.

$$m = (\text{Change in MPF})/(\text{Change in time}) \quad \text{Equation 25}$$

The change in time is the length of time required before slow-twitch fibers become the primary force behind an activity. This is the amount of time until the inflection point.

Work done by slow-twitch fibers during an activity can be calculated by taking the integral of the rectified sEMG graph, from the inflection point until the final point. Then, muscular work estimation index (MWEI) average conversion factor is utilized to convert area under the curve to work done by Equation 26.

$$\text{Work Done by Slow-Twitch} = \int_{Time\ of\ Inflection}^{Time\ of\ Final} \text{MWEI}_{slow-twitch} = CF_{average} \text{sEMG} \quad \text{Equation 26}$$

Figure 10C:
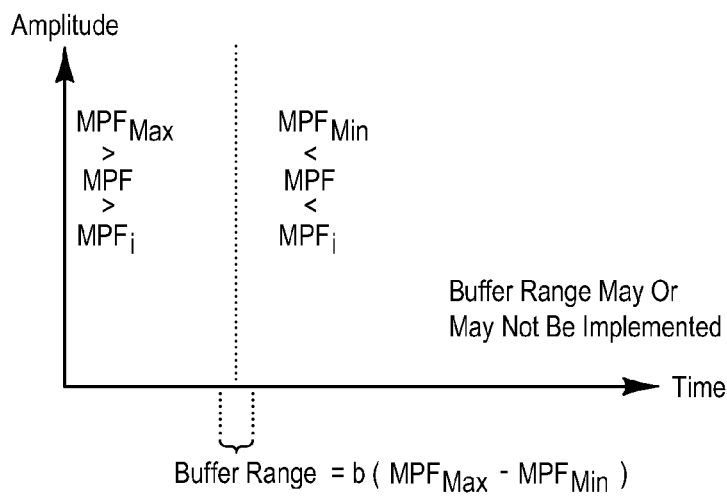
FIG. 10C is a depiction of the amplitude vs. time graph where a buffer range is optionally used to account for errors in determining the inflection point.

The area under the curve of the rectified sEMG graph can also be converted to calories burned by the slow-twitch fibers by conversion through skeletal muscle calorie index (SMCI) database referencing, if desired. Finally, the STMI may be configured with a buffer range. A buffer range may be necessary in order to account for errors in the measurement as shown in FIG. 10C.

Fast-Twitch Muscle Index (FTMI)

The fast-twitch muscle index (FTMI) includes a family of indexes which are closely related to the STMIs; however, as expected, a band-pass filter is created for all data points after detection of the inflection point, rather than for all points before the inflection point in the STMI method.

Like other metrics aforementioned, FTMI is determined through FTMI protocol by selecting the FTMI protocol. The FTMI protocol gathers sEMG data and then measures the inflection point. The inflection point is determined on the graph of sEMG amplitude versus time or the corresponding MPF versus time. The inflection point represents the point at which fast-twitch muscle fibers become a secondary force to slow-twitch muscle fibers.

As shown in FIG. 10A, the maximum amplitude of fast-twitch muscle fiber activation is determined, which is the maximum amplitude of the rectified sEMG graph observed prior to the inflection point. It should be noted that the figures for the slow-twitch protocols can be used for fast-twitch protocols.

Also, an average amplitude of fast-twitch muscle fiber activation can be determined. This is the average amplitude of the rectified sEMG graph from the start of the session until the inflection. The rate of fatigue of fast-twitch muscle fibers can also be determined, which is calculated by looking at the slope of a line which is fit to the graph of MPF versus time, from the start point until the point of inflection as expressed in Equation 25 above. The work done by fast-twitch fibers during an activity can be calculated by taking the integral of the rectified sEMG graph, from the first point until the inflection point. Then, the MWEI and associated conversion factor, is utilized to convert area under the curve to work done as represented by Equation 27.

$$\text{Work Done by Fast Twitch} = \text{MWEI}_{fast-twitch} = \text{CF}_{MWEI\ average} \times (\int_{Time\ of\ Start}^{Time\ of\ Inflection} \text{sEMG}) \quad \text{Equation 27}$$

Also, the area under the curve of the rectified sEMG graph can be converted to calories burned by the slow-twitch fibers by conversion through SMCI database referencing, if desired. Finally, the FTMI may be configured with a buffer range. A buffer range may be necessary in order to account for errors in the measurement.

Personal Multidimensional Fitness Index (PMFI)

The personal multidimensional fitness index (PMFI) is a multi-factor metric which describes the fitness level of an individual at a particular point in time, as shown in FIG. 11A. In addition, PMFI can describe the fitness level of different individuals over time as shown by FIG. 11B. While there are many fitness metrics in use today, this metric differentiates itself by including sEMG-based factors such as the MFOI.

Like other metrics aforementioned, PMFI is determined through PMFI protocol by selecting the PMFI protocol. The PMFI protocol gathers data related to some of the aforementioned metrics, and aggregates the resultant values to create PMFI.

In order to calculate the PMFI, an individual can perform an activity for a length of time that is non-negligible (more than a few minutes). For example, in one embodiment, a runner might run for 30 minutes or whatever their typical exercise might be. In this manner, the MFOI is calculated, which has a negative value. The less in shape an individual's muscles are, more negative the MFOI becomes. The closer to 0 the slope of the graph of MPF over time is, the more in shape an individual's muscles are.

Another factor may be based on MASI. For the activity performed over a length of time, the symmetry index is also recorded (e.g., MASI). The closer MASI is to 0, the more in shape the subject is.

Likewise, the HR of the individual is measured during the activity. At a given age, each individual has a target HR for physical activity which involves a cardiovascular component (e.g., basically all physical activities). The closer to the target HR an individual is, the more in-shape they are, cardiovascularly speaking.

Also, the BMI of an individual can be utilized in the PMFI metric. It can be estimated in a number of ways, including a simplistic estimation based on the subject's height and weight. The closer to their ideal BMI a subject is, the more in-shape the subject is. In other words, the closer to zero the difference between ideal BMI and actual BMI is zero, the more in-shape the individual is.

Additionally, maximum oxygen consumption (e.g., VO2_max) can be utilized as well. This is a derivative metric, which can be estimated based on max HR during exercise. Since the ideal VO2_max for any individual can be determined by HR, the close to zero the difference is between ideal VO2_max and actual VO2_max, the more in-shape the individual is.

PMFI is calculated by Equation 28 or a normalized version thereof.

$$\text{PMFI} = n - \{(|\text{MFOI}| + \text{MASI} + |(\text{HR\_ideal} - \text{HR\_actual})| + |(\text{BMI\_ideal} - \text{BMI\_actual})| + |(\text{VO2Max\_ideal} - \text{VO2Max\_actual})|\} \quad \text{Equation 28}$$

Here, "n" is a non-critical constant determined experimentally. Depending on natural variation in PMFI in a given population, "n" can be set to provide a spread with a range that is intuitive to subjects who wish to look at the number and quickly assess their personal fitness level. In the above PMFI definition, each term has been set up in such a way so that if the subject is in ideal shape, PMFI will be close in range to the constant "n." Alternatively, if the subject is out of shape, PMFI will be comparatively far from the constant "n."

In one embodiment, the invention described herein can be implemented with the sensors or systems described in U.S. Provisional Application Nos. 61/385,048 and 61/514,148 and U.S. patent application Ser. No. 13/239,033, the serial number to be inserted here after the filing thereof). Additionally, the invention described herein can be implemented with metrics and algorithms described in U.S. Provisional Application No. 61/385,046 and U.S. patent application Ser. No. 13/239,105, the serial number to be inserted here after the filing thereof). Also, the invention described herein can be implemented with methods of promoting fitness described in U.S. Provisional Application No. 61/385,053 and U.S. patent application Ser. No. 13/239,079, the serial number to be inserted here after the filing thereof). Further, the invention described herein can be implemented with graphing methods described in U.S. Provisional Application No. 61/385,049. Also, the invention described herein can be implemented with the multi-functional carrying case and associated biometric sensors and transceivers described in U.S. Provisional Application No. 61/385,051. The invention described herein can be implemented with the devices, systems, and/or methods described in U.S. Pat. Nos. 7,593,769 and 7,809,435. The patents and patent applications recited herein are incorporated herein by specific reference in their entirety.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, hand-held computing systems and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical subject interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 6:
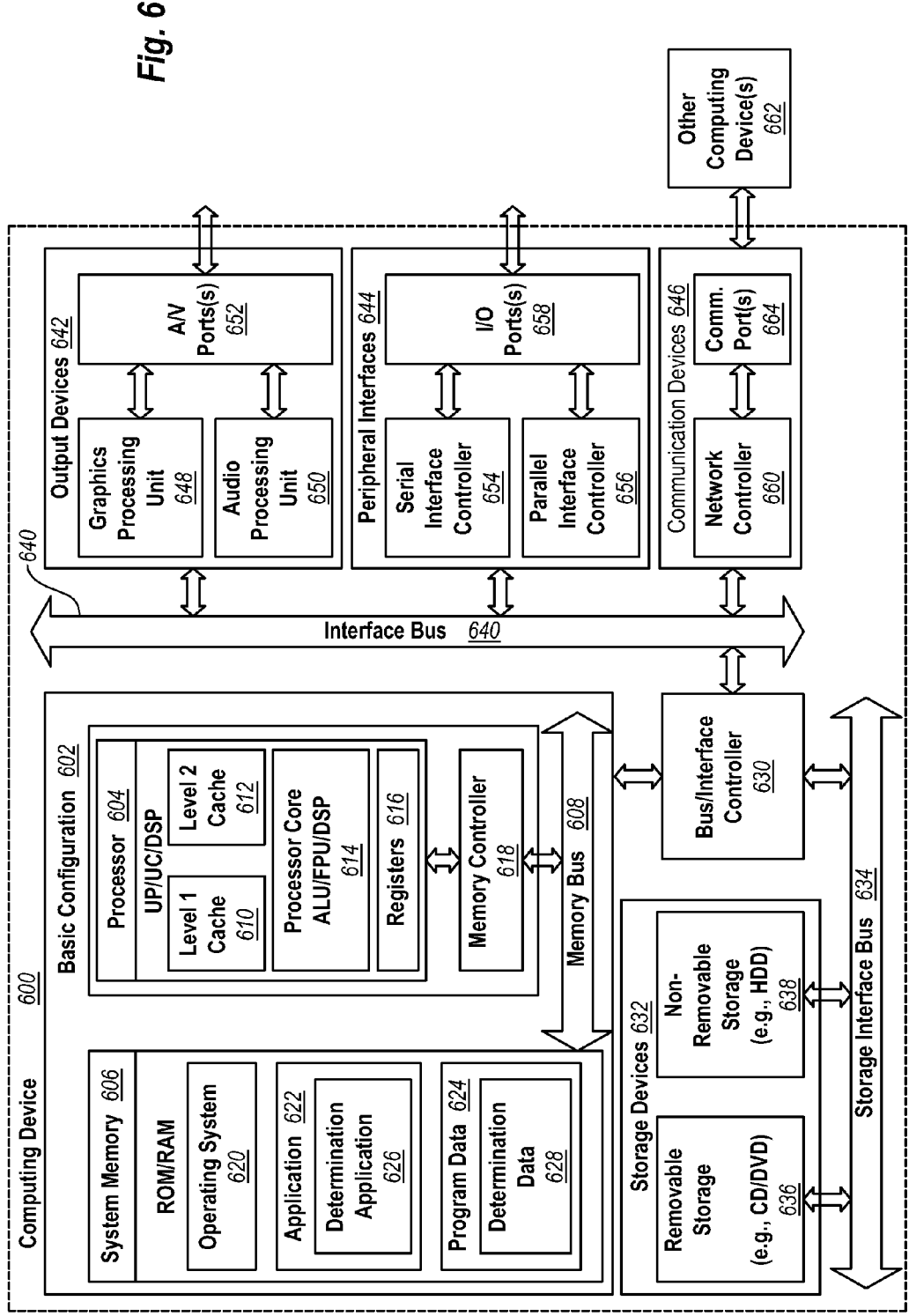
FIG. 6 is a depiction of a computing system that, in one embodiment, may be used to perform the methods disclosed herein.

FIG. 6 shows an example computing device 600 that is arranged to perform any of the computing methods described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (µP), a microcontroller (µC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on operating system 620 such that the work performed by untrusted computing nodes can be verified as described herein. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

What is claimed is:

1. A muscle assessment method comprising:
physically coupling:
   at least one surface electromyometry (sEMG) sensor to a subject;
   at least one temperature sensor to the subject; and
   at least one heart rate sensor to the subject;
   the at least one sEMG sensor, at least one temperature sensor, and at least one heart rate sensor also being communicably coupled to a computing system;
the computing system gathering data from the at least one sEMG sensor, at least one temperature sensor, and at least one heart rate sensor physically coupled to the subject while the subject is engaged in a muscle activity;
the computing system monitoring and/or recording relevant data of the subject engaged in the muscle activity from the at least one sEMG sensor, at least one temperature sensor, and at least one heart rate sensor physically coupled to the subject;
determining at least one muscle fatigue onset index (MFOI), the determining of the at least one MFOI comprising:
   selecting a MFOI protocol;
   the computing system plotting sEMG mean power frequency (MPF) amplitude data points gathered over a period of time to a line;
   the computing system determining the slope of the line as the rate of muscle fatigue; and the computing system determining the at least one MFOI from the slope of the line as the rate of muscle fatigue from the plot of the sEMG MPF amplitude data points gathered over the period of time to the line; and the computing system using the MFOI to estimate how quickly the subject's muscles will become fatigued.

2. The method of claim 1, further comprising: the computing system plotting sEMG amplitude data points gathered at set time intervals.

3. The method of claim 1, further comprising: the computing system plotting maximum sEMG amplitude data points gathered continuously.

4. The method of claim 1, further comprising: the computing system plotting average sEMG amplitude data for an epoch gathered continuously.

5. The method of claim 1, comprising determining chronic muscle overuse index (CMOI), the CMOI determining comprising:
- selecting CMOI protocol;
- performing a calibration activity;
- plotting sEMG amplitude data points gathered over a period of time to a curve to establish a dataset;
- referencing a database to determine a related average dataset;
- determining CMOI based on the relationship between the dataset and the related average dataset; and
- determining a conversion factor based on the ratio of the rate of change for non-ideal conditions to the rate of change for ideal conditions.

6. The method of claim 5, further comprising projecting estimated chronic muscle overuse, the projecting estimated chronic muscle overuse comprising:
- applying a conversion factor to project estimated amplitude for muscle exhaustion for a given activity; and
- determining a time associated with the estimated amplitude for muscle exhaustion.

7. The method of claim 5, further comprising determining a warm up index (WUI), the determining the WUI comprising:
- recording initial sEMG amplitude as an initial WUI;
- recording the corresponding frequency;
- referencing a database to determine a related average dataset;
- determining a second WUI based on the related average dataset; and
- determining a third WUI based on the user input of a related average dataset.

8. The method of claim 1, further comprising determining chronic muscle overuse index (CMOI), the determining CMOI comprising:
- selecting CMOI protocol;
- performing a calibration activity;
- plotting sEMG frequency data points gathered over a period of time to a line;
- referencing a database to determine a related average dataset;
- determining CMOI based on the relationship of the subject data and the related average dataset; and
- determining a conversion factor based on the ratio of the rate of change for non-ideal conditions to the rate of change for ideal conditions.

9. The method of claim 8, further comprising projecting estimated chronic muscle overuse, the projecting estimated chronic muscle overuse comprising:
- applying a conversion factor to project an estimated frequency for muscle exhaustion for a given activity; and
- determining a time associated with the estimated frequency for muscle exhaustion.

10. The method of claim 8, further comprising determining safety zones, the determining safety zones comprising:
- calculating the amplitude/MPF ranges for each zone; and
- calculating the time associated with the boundaries for each zone.

11. The method of claim 1, further comprising determining an impulsive muscle overuse index (IMOI), the IMOI determining comprising:
- selecting IMOI protocol;
- performing a calibration activity in a semi-controlled environment;
- recording pseudo maximum voluntary contractions (PMVC) data;
- associating PMVC data with known maximum voluntary contraction (MVC) data in a controlled environment into a combined database;
- referencing the combined database to determine a relate average dataset;
- determining IMOI based on an safe threshold amplitude of the related average dataset; and
- determining a conversion factor based on the ratio of the MVC data to the PMVC data.

12. The method of claim 11, further comprising projecting estimated impulsive muscle overuse, the projecting estimated impulsive muscle overuse comprising:
- applying a conversion factor to project a safe threshold estimated amplitude for a given activity; and
- determining a time associated with the safe threshold estimated amplitude for muscle exhaustion.

13. The method of claim 11, further comprising determining a weighted IMOI, the determining of the weighted IMOI comprising:
- determining a safety constant as some number less than 1 and more than zero; and
- multiplying IMOI by the safety constant to determine a weighted IMOI.

14. The method of claim 1, further comprising determining muscular work estimation index (MWEI), the determining of the muscular work estimation indes comprising:
- selecting MWEI protocol;
- performing a calibration activity in a semi-controlled environment;
- recording sEMG amplitude data and work data for associated activity;
- plotting data points on respective graphs;
- finding the integrated sEMG amplitude value and the sum of the work output value;
- determining a conversion factor based on the ratio of work output value to the integrated sEMG value;
- storing the data and associated conversion factor in a database;
- referencing the combined database for a related average dataset conversion factor to new user sEMG data; and
- determining MWEI by multiplying a new user sEMG data by the related average dataset conversion factor.

15. The method of claim 1, further comprising determining skeletal muscle calorie index (SMCI), the determining SMCI comprising:
- selecting SMCI protocol; performing a calibration;
- recording both sEMG amplitude data and caloric expenditure data for associated activity;
- plotting data points on respective graphs;
- determining the integrated sEMG amplitude value and the total caloric expenditure value;

determining a conversion factor based on the ratio of the total caloric expenditure value to the integrated sEMG amplitude value;
referencing a database to determine a related average dataset;
determining an average conversion factor based on the ratio of a related sum dataset to the total number of datasets sampled; and
determining SMCI by multiplying a the average conversion factor by the sum integrated sEMG data associated with the related sum dataset.

16. The method of claim 15, further comprising:
a conversion factor for a single muscle; and
a conversion factor for at least one muscle or muscle group.

17. The method of claim 1, further comprising determining cardiovascular muscle calorie index (CMCI), the determining CMCI comprising:
selecting CMCI protocol;
performing a calibration;
recording both sEMG amplitude data and heart rate (HR) data for associated activity;
plotting data for sEMG data;
referencing HR data with a known database to determine a first estimate of calories burned (CHR);
referencing the integrated sEMG data with SMCI to determine a second estimate of calories burned (CRS); and
determining CMCI by adding CHR to CRS and dividing by 2.

18. The method of claim 17, further comprising determining a weighted CMCI, the determining the weighted CMCI comprising:
multiplying CHR by a first weighted constant between zero and one to establish a CHR weighted value;
multiplying CRS by a second weighted constant between zero and one to establish a CRS weighted value;
wherein the sum of the first and second weighted constant equals 1; and
determining the weighted CMCI by adding the CHR weighted value to the CRS weighted value.

19. The method of claim 1, further comprising determining muscle activation symmetry index (MASI) and muscle condition, the determining MASI comprising:
selecting MASI protocol;
performing a calibration;
recording rectified sEMG amplitude data for a right side of a symmetrical muscle or muscle group;
recording rectified amplitude data for a left side of a symmetrical muscle or muscle group;
determining MASI by subtracting rectified right-side amplitude from rectified left-side amplitude;
referencing a database to determine an average related dataset known as normalized muscle activation symmetry index (NMASI); and
determining the condition of a symmetrical muscle group by comparing MASI to NMASI.

20. The method of claim 19, further comprising determining muscle condition in symmetrical muscle groups, the determining muscle condition in symmetrical muscle groups comprising:
designating muscle condition as normal if MASI<NMASI; and
designating a muscle condition as abnormal if MASI>NMASI.

21. The method of claim 19, further comprising determining MASI, the determining MASI comprising:
measuring MASI over time for the same individual and muscle or muscle group; and
averaging MASI over time by calculating the sum and dividing by the number of samples.

22. The method of claim 14, further comprising determining muscle work difference index (MWDI), the determining MWDI comprising:
performing a MWEI protocol for a plurality of muscles or muscle groups;
determining at least a first value and a second value representing the work done for each muscle or muscle group;
subtracting the at least first value from the at least second value to determine MWDI;
referencing a database to determine an average related dataset known as normalized muscle work difference index (NMWDI); and
determining the condition of a muscle or muscle group by comparing a MWDI to NMWDI.

23. The method of claim 22, further comprising determining muscle condition, the determining muscle condition comprising:
designating muscle condition as normal if MWDI≤NMWDI; and
designating a muscle condition as abnormal if MWDI>NMWDI.

24. The method of claim 1, further comprising determining slow-twitch muscle indexes (STMI), the determining STMI comprising:
selecting STMI protocol;
performing a calibration activity;
recording sEMG amplitude data for the subject engaged in the activity; plotting data gathered on an amplitude versus time graph;
noting the inflection point;
determining a corresponding inflection point on an MPF versus time graph;
filtering out all data coming before the inflection point to determine activity dominated by slow-twitch muscle fibers; and
calculate one or more of the maximum amplitude of slow-twitch fiber activity, average amplitude of slow-twitch muscle fibers, the rate of fatigue of slow-twitch fibers, the length of time required before slow-twitch fibers become the primary force behind the activity; and/or
work done by slow-twitch fibers during the activity.

25. The method of claim 1, further comprising determining fast-twitch muscle indexes (FTMI), the determining FTMI comprising:
selecting FTMI protocol;
performing a calibration activity;
recording sEMG amplitude data for a subject engaged in the activity;
plotting data gathered on an amplitude versus time graph;
noting the inflection point;
determining a corresponding inflection point on an MPF versus time graph;
filtering out all data coming after the inflection point to determine activity dominated by slow-twitch muscle fibers; and
calculate one or more of the maximum amplitude of fast-twitch fiber activity, average amplitude of fast-twitch muscle fibers, the rate of fatigue of fast-twitch fibers, the length of time fast-twitch fibers are the primary force behind the activity; and/or
work done by fast-twitch fibers during the activity.

26. The method of claim 25, further comprising determining caloric expenditure, the determining caloric expenditure comprising:

determining caloric expenditure of slow-twitch fiber activity by converting the integral sEMG data to caloric expenditure with SMCI protocol.

27. The method of claim 1, further comprising determining personal multidimensional fitness index (PMFI), the determining PMFI comprising:
   selecting PMFI protocol;
   gathering a plurality of index values;
   determining an actual first value from a subject's activity related to the probability of the individual to experience muscle fatigue;
   determining an actual second value from a subject's activity related to the proximity of that individual's heart rate to match a known target heart rate;
   determining an actual third value from a subject's activity related to the proximity of an individual's body-mass index (BMI) to match a known target heart rate;
   determining an actual fourth value from a subject's activity related to the proximity of an individual's maximal oxygen intake (VO2_max) data point to match a known target VO2_max data point;
   summing at least two of the absolute actual values of the first, second, third, and fourth values to create a resulting actual value; and subtracting the actual value from an ideal value resulting in a multidimensional fitness metric.

28. A muscle assessment method comprising:
   physically coupling:
      at least one surface electromyometry (sEMG) sensors to a subject;
      at least one temperature sensor to the subject; and
      at least one heart rate sensors to the subject;
      the at least one sEMG sensor, at least one temperature sensor, and at least one heart rat sensor also being communicably coupled to a computing system;
   the computing system gathering data from the at least one sEMG sensor, at least one temperature sensor, and at least one heart rate sensor while the subject is engaged in a muscle activity;
   the computing system monitoring and/or recording relevant data of the subject engaged in the muscle activity; and
   determining at least one muscle fatigue onset index (MFOI), the determining of the MFOI comprising:
      selecting a MFOI protocol;
      the computing system plotting sEMG mean power frequency (MPF) amplitude data points gathered over a period of time to a line;
      the computing system determining the slope of the line as the rate of muscle fatigue;
      the computing system determining the at least one MFOI from the slope of the line as the rate of muscle fatigue from the plot of the sEMG MPF amplitude data points gathered over the period of time to the line; and
   the computing system comparing the MFOI to a set of MFOI from other subjects to estimate how physically fit the subject is.

29. The method of claim 28, further comprising:
   determining variables for use in determining the MFOI including:
      a frequency sampling rate (FSR); and
      time of activity (AT).

30. The method of claim 29, further comprising the computing system calculating a quantity of total samples (QS) for calculating the MFOI as defined by the following equation:

$$QS=(AT/FSR)+1.$$

* * * * *